United States Patent
Stocking et al.

(10) Patent No.: US 11,236,079 B2
(45) Date of Patent: Feb. 1, 2022

(54) MORPHOLINE DERIVATES AS INHIBITORS OF VPS34

(71) Applicant: Neuropore Therapies, Inc., San Diego, CA (US)

(72) Inventors: Emily M. Stocking, Encinitas, CA (US); Wolfgang J. Wrasidlo, La Jolla, CA (US)

(73) Assignee: Neuropore Therapies, Inc., San Diego, CA (US)

( * ) Notice: Subject to any disclaimer, the term of this patent is extended or adjusted under 35 U.S.C. 154(b) by 0 days.

(21) Appl. No.: 17/046,750

(22) PCT Filed: Apr. 9, 2019

(86) PCT No.: PCT/US2019/026646
§ 371 (c)(1),
(2) Date: Oct. 9, 2020

(87) PCT Pub. No.: WO2019/199874
PCT Pub. Date: Oct. 17, 2019

(65) Prior Publication Data
US 2021/0163467 A1  Jun. 3, 2021

Related U.S. Application Data

(60) Provisional application No. 62/655,723, filed on Apr. 10, 2018.

(51) Int. Cl.
| C07D 417/12 | (2006.01) |
| C07D 417/04 | (2006.01) |
| C07D 417/10 | (2006.01) |
| C07D 285/135 | (2006.01) |
| C07D 285/08 | (2006.01) |
| C07D 277/40 | (2006.01) |

(52) U.S. Cl.
CPC ......... C07D 417/12 (2013.01); C07D 285/08 (2013.01); C07D 285/135 (2013.01); C07D 417/04 (2013.01)

(58) Field of Classification Search
CPC .. C07D 417/12; C07D 417/04; C07D 417/10; C07D 285/135; C07D 285/08; C07D 277/40
See application file for complete search history.

(56) References Cited

U.S. PATENT DOCUMENTS

2011/0230476 A1   9/2011 Niu et al.

FOREIGN PATENT DOCUMENTS

| WO | WO-2007/084786 | 7/2007 |
| WO | WO-2009/066084 | 5/2009 |
| WO | WO-2012/135160 | 10/2012 |
| WO | WO-2017/140843 | 8/2017 |
| WO | WO-2017/210545 | 12/2017 |
| WO | WO-2019/199874 | 10/2019 |

OTHER PUBLICATIONS

Backer et al., "The regulation and function of Class III PI3Ks: novel roles for Vps34," Biochem J (2008) 410(1):1-17.
Bagshawe, "Antibody-Directed Enzyme Prodrug Therapy: A Review," Drug Dev. Res. (1995) 34:220-230.
Baptiste et al., "A highly potent and selective Vps34 inhibitor alters vesicle trafficking and autophagy," Nature Chemical Biology (2014) 10(12):1013-1019.
Berge et al., "Pharmaceutical Salts," J. Pharm. Sci., 1977, 66, 1-19.
Bilanges et al., "Vps34 PI 3-kinase inactivation enhances insulin sensitivity through reprogramming of mitochondrial metabolism," Nature Communications (2017) 8:1804.
Bodor, "Novel Approaches to the Design of Safer Drugs: Soft Drugs and Site-Specific Chemical Delivery Systems," Adv. Drug Res. (1984) 13:255-331.
Brooks, D.J., "Positron Emission Tomography and Single-Photon Emission Computed Tomography in Central Nervous System Drug Development," NeuroRx 2005, 2(2), 226-236.
Castino et al., "Inhibition of PI3k Class III-Dependent Autophagy Prevents Apoptosis and Necrosis by Oxidative Stress in Dopaminergic Neuroblastoma Cells," Toxicological Sciences (2010) 117(1):152-162.
Chude et al., "Targeting Autophagy in Cancer: Update on Clinical Trials and Novel Inhibitors," Int J Mol Sci (2017) 18(6):1279.
Goberdhan et al., "Amino acid sensing and mTOR regulation: inside or out?" Biochem Soc Trans (2009) 37(1):248-252.
Hawkins et al., "PI3K signalling in inflammation," Biochim Biophys Acta (2015) 1851(6):882-897.
Mathew et al., "Role of autophagy in cancer," Nat Rev Cancer (2007) 7(12):961-967.
Okkenhaug, "Signaling by the phosphoinositide 3-kinase family in immune cells," Annu Rev Immunol (2013) 31:675-704.
Pasquier et al., "SAR405, a PIK3C3/Vps34 inhibitor that prevents autophagy and synergizes with MTOR inhibition in tumor cells," Autophagy (2015) 11(4):725-726.

(Continued)

Primary Examiner — Laura L Stockton
(74) Attorney, Agent, or Firm — Morrison & Foerster LLP

(57) ABSTRACT

The present disclosure relates to thiazole- or diathiazole-substituted aryl and heteroaryl compounds (I), pharmaceutical compositions containing them, and methods of using them, including treatment of disorders or disease related to regulation of the Vps34/PI3K III signaling pathway.

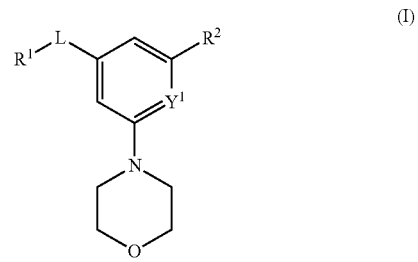

(I)

34 Claims, No Drawings

(56) References Cited

OTHER PUBLICATIONS

Shan et al., "Prodrug strategies based on intramolecular cyclization reactions," J. Pharm. Sci. (1997) 86(7):765-767.
Stein, "Prospects for phosphoinositide 3-kinase inhibition as a cancer treatment," Endocrine-related Cancer (2001) 8:237-248.

MORPHOLINE DERIVATES AS INHIBITORS OF VPS34

CROSS-REFERENCE TO RELATED APPLICATIONS

This application is a national stage application under 35 U.S.C. § 371 of International Application No. PCT/US2019/026646, filed internationally on Apr. 9, 2019, which claims priority to U.S. Provisional Application No. 62/655,723, filed Apr. 10, 2018, entitled "MORPHOLINE DERIVATES AS INHIBITORS OF VPS34," the content of which is hereby incorporated by reference in its entirety for all purposes.

TECHNICAL FIELD

The present disclosure relates to thiazole- or diathiazole-substituted aryl and heteroaryl compounds, pharmaceutical compositions containing them, and methods of using them, including treatment of disorders or diseases related to regulation of the Vps34/PI3K III signaling pathway.

BACKGROUND

Vps34 (vascular protein sorting 34) is a class III member of the PI3K (phosphatidylinositol 3-kinase) family of lipid kinases and is involved in the regulation of numerous cellular function. Vps34 is the only PI3-kinase expressed in all eukaryotic cells. It was initially identified in yeast and found evolutionarily conserved though mammals. In humans, hVPS34 is encoded by the PIK3C3 gene. Vps34 phosphorylates phosphatidylinositol (PI) to form phosphatidylinositol 3-phosphate (PI3P) at the pre-autophagosome or endosome leading to the recruitment of FYVE and PX domain containing proteins (Hawkins P. T., Stephens L. R. PI3K signaling in inflammation. Biochim. Biophys. Acta. 2015; 1851:882-897; Okkenhaug K. Signaling by the phosphoinositide 3-kinase family in immune cells. Annu. Rev. Immunol. 2013; 31:675-704; Backer J. M. Biochem. J. 2008; 410:1-17). Vps34 associates with the protein kinase Vps15 in different protein complexes, and plays an important role in membrane trafficking and protein sorting pathways. Unlike other PI3Ks, the substrate specificity of Vps34 is limited to phosphatidylinositol. This property distinguishes it from class I and II enzymes, which can phosphorylate more extensively depending on the isoform. PI3P produced by Vps34 is critical for autophagosome and phagosome maturation as well as NOX2 mediated ROS production, thereby playing a key role in autophagy, as well as pathogen uptake and killing by innate immune cells.

The initial function of Vps34 is the regulation of vesicular trafficking in the endosome/lysosome, where it is involved in the recruitment of proteins, containing binding motifs to intracellular membranes. Inhibiting Vps34 can result in lysosomal function impairment, affecting vesicle trafficking between late endosome and the lysosome (Pasquier B. Autophagy. 2015; 11:725-726). Vps34 activity is required for autophagy in yeast and has been strongly implicated in this process in mammals. Autophagy is a process in which cellular components are engulfed and degraded within double-membrane vesicles (autophagosomes) and has an important role in the response to oxidative damage. The interaction of Vps34 with the autophagy gene beclin1 is critical for autophagosome biogenesis, maturation and apoptosis. Inhibition of this step with Vps34 inhibitors can prevent the formation of autophagy vesicles (Chude, C. I. et al. (2017). Targeting Autophagy in Cancer: Update on Clinical Trials and Novel Inhibitors. Int. J. Mol. Sci., 18(6): pages 1279-1289). Vps34 has also been implicated in amino acid sensing and has been suggested to regulate mTOR in mammalian cell culture (Goberdhan, D. C. I.; et al. (2009). Biochem. Soc. Trans.; 37(Pt 1): pages 248-252).

Irregular activities of PI3-kinases are observed in numerous human pathological conditions including diabetes, diabetes-associated cardiovascular disease, polycystic ovarian syndrome, cancer, neuro-inflammation and ischemic stroke. As a potential diabetes therapy, inhibition of Vps34 can enhance glucose tolerance and insulin sensitivity by reducing glucose production in the liver and stimulating glucose uptake in muscle. In vitro, treatment of mytotubes, hepatocytes and myoblast cells with a Vps34 inhibitor activated the AMPK pathway (increased levels of pAMPK$^{T172}$ and pACC$^{S79}$) thereby effecting cellular energy homeostasis. In vivo, treatment of HFD-fed mice with a selective Vps34 antagonist showed improvement in both glucose tolerance and insulin sensitivity (as assessed by GTT and ITT). (Bilanges, B. et al., (2017). Vps34 PI 3-Kinase Inactivation Enhances Insulin Sensitivity Through Reprogramming of Mitochondrial Metabolism. Nature Comm. 8 (1): Article no.: 1804). In cancer, Vps34 inhibitors may prove useful because, unlike PI3K class I and II enzyme inhibitors that lead to the induction of autophagy, Vps34 inhibition leads to the abrogation of autophagy. Autophagy may prolong the survival of cancer cells defective in apoptosis by protecting them from metabolic stress. Inhibiting autophagy and sensitizing apoptosis-resistant cells to metabolic stress has potential as a tumor therapy regimen (Mathew et al., (2007). Role of autophagy in cancer. Nat Rev Cancer, (12), pages 961-967; Stein et al., (2001). Prospects for phosphoinositide 3-kinase inhibition as a cancer treatment. Endocrine-Related Cancer (8), pages 237-248). Vps34 inhibition may also be cyto-protective in stressful conditions such as ischemia-reperfusion. Inactivation of the Vps34/phosphatydil-inositol-3-phosphate kinase (PI3K) III signaling pathway, either by pharmacologic inhibition with 3-methyladenine (3MA) or by transgenic expression of a dominant-negative Vps34, prevented onset of autophagy and protected dopaminergic neuroblastoma cells (SH-Sy5y) from $H_2O_2$ toxicity (Castino et al., 2010. Inhibition of PI3k Class III-Dependent Autophagy Prevents Apoptosis and Necrosis by Oxidative Stress in Dopaminergic Neuroblastoma Cells. Toxicological Sciences, (117), 1, pages 152-162).

SUMMARY

In one aspect, provided is a compound of Formula I:

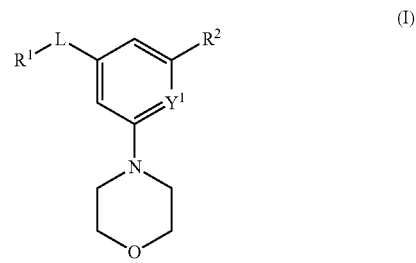

wherein
$R^1$ is $C_6$-$C_{14}$ aryl, 5- to 10-membered heteroaryl, $C_3$-$C_6$ cycloalkyl, or 4- to 10-membered heterocycloalkyl, wherein the $C_6$-$C_{14}$ aryl, 5- to 10-membered heteroaryl, $C_3$-$C_6$ cycloalkyl, or 4- to 10-membered heterocycloalkyl of $R^1$ are each unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl;

L is —S(O)$_2$—, —O—, —C(O)— or —CH$_2$—;

$Y^1$ is CH or N;

$R^2$ is a 5-membered heteroaryl or a 5-membered heterocycloalkyl, wherein the 5-membered heteroaryl and 5-membered heterocycloalkyl of $R^2$ are each unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl; and $R^a$, $R^b$, $R^c$, $R^d$, $R^e$, and $R^f$ are each independently H or $C_{1-4}$ alkyl;

wherein when L is —S(O)$_2$— and $Y^1$ is N, $R^1$ is not 4,4-difluoro-piperidin1-yl;

or a pharmaceutically acceptable salt thereof.

In some embodiments of the compound of the formula (I), $R^1$ is $C_6$-$C_{14}$ aryl or 4- to 10-membered heterocycloalkyl. In some embodiments, $R^1$ is phenyl. In some embodiments, $R^1$ is a 5- or 6-membered heterocycloalkyl heterocycloalkyl. In some embodiments, $R^1$ is tetrahydrofuranyl, tetrahydropyranyl, pyrrolidinyl, piperidinyl, piperazinyl, or morpholinyl. In some embodiments, $R^1$ is tetrahydrofuranyl. In some embodiments, $R^1$ is tetrahydropyranyl. In some embodiments, $R^1$ is tetrahydrofuran-3-yl. In other embodiments, $R^1$ is tetrahydropyran-4-yl.

In some embodiments of the compound of the formula (I), L is —S(O)$_2$—. In some embodiments, L is —O—. In some embodiments, L is —C(O)—. In some embodiments, L is —CH$_2$—. In some embodiments, $Y^1$ is CH. In some embodiments, $Y^1$ is N.

In some embodiments of the compound of the formula (I), $R^2$ is a 5-membered heteroaryl ring, wherein the 5-membered heteroaryl ring is substituted with one or more substituents selected from the group consisting of $C_{1-6}$ alkyl, $C_{1-6}$ haloalkyl and NR$^e$R$^f$, wherein R$^e$ and R$^f$ are independently H or $C_{1-4}$ alkyl. In some embodiments, $R^2$ is thiazolyl or thiadiazolyl substituted with one or more substituents selected from the group consisting of $C_{1-6}$ alkyl, $C_{1-6}$ haloalkyl and NR$^e$R$^f$, wherein R$^e$ and R$^f$ are independently H or $C_{1-4}$ alkyl. In certain embodiments, $R^2$ is thiazolyl or thiadiazolyl substituted with one or more substituents selected from the methyl, CF$_3$ and NH$_2$.

In some embodiments, $R^2$ is:

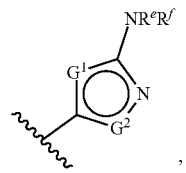

wherein
$G^1$ is S or N;
$G^2$ is CR$^3$, S, or N;
$R^3$ is H, $C_{1-6}$ alkyl or $C_{1-6}$ haloalkyl; and
R$^e$ and R$^f$ are independently H or $C_{1-4}$alkyl.

In some embodiments, $G^1$ is S. In some embodiments, $G^1$ is N. In some embodiments, $G^2$ is CR$^3$. In some embodiments, $R^3$ is H. In some embodiments, $R^3$ is $C_{1-6}$ alkyl. In other embodiments, $R^3$ is $C_{1-6}$ haloalkyl. In some embodiments, $G^2$ is S. In some embodiments, wherein $G^2$ is N. In some embodiments, $G^1$ is S and $G^2$ is CR$^3$, wherein $R^3$ is H, $C_{1-6}$ alkyl or $C_{1-6}$ haloalkyl. In some embodiments, $G^1$ is S and $G^2$ is CH. In some embodiments, $G^1$ is S and $G^2$ is CC$_{1-6}$ alkyl. In other embodiments, $G^1$ is S and $G^2$ is CC$_{1-6}$ haloalkyl. In some embodiments, $G^1$ is N and $G^2$ is S. In other embodiments, $G^1$ is S and $G^2$ is N. In some of any of the foregoing embodiments, R$^e$ and R$^f$ are both H. In some of any of the foregoing embodiments, one of R$^e$ and R$^f$ is $C_{1-4}$alkyl and the other is H. In other embodiments, R$^e$ and R$^f$ are both $C_{1-4}$alkyl.

Also provided are compounds selected from the group consisting of:

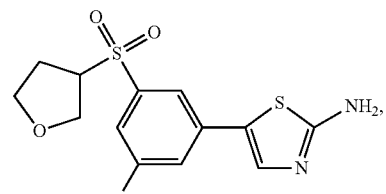

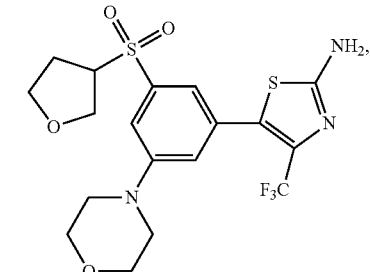

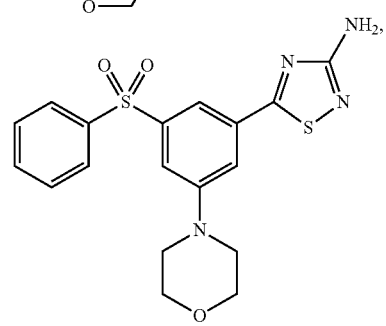

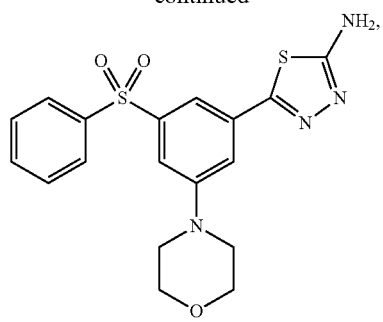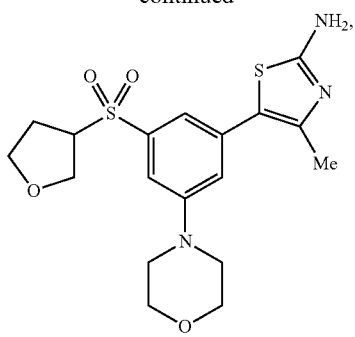

-continued
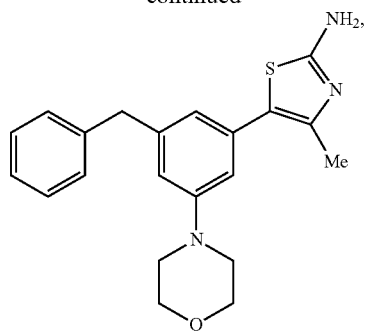
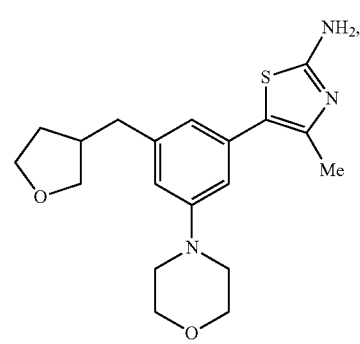
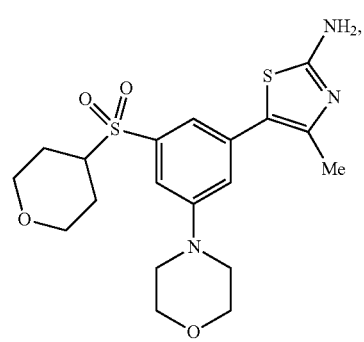
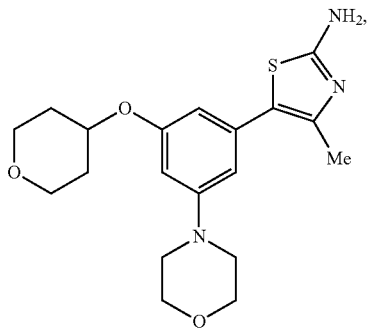
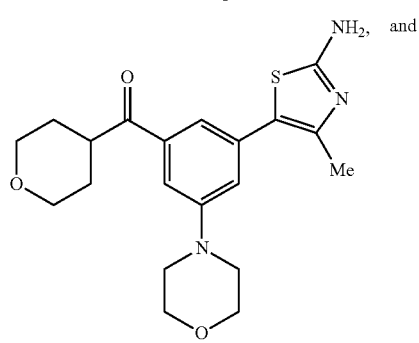
-continued
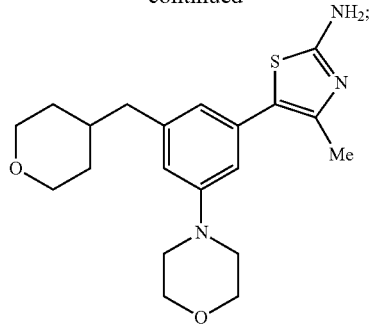
or a pharmaceutically acceptable salt thereof.
In some embodiments, the compound is selected from the group consisting of:
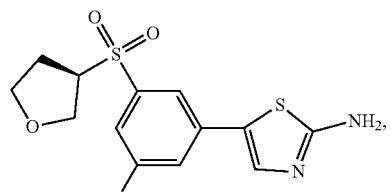
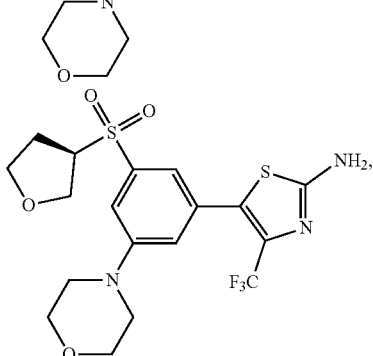
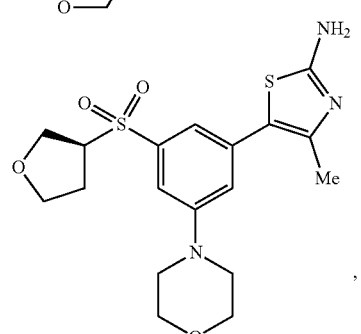
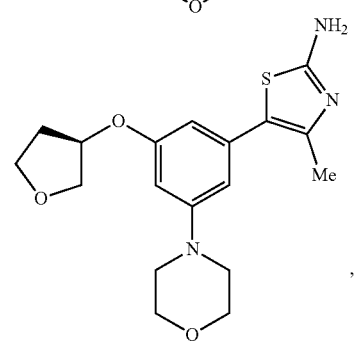

-continued
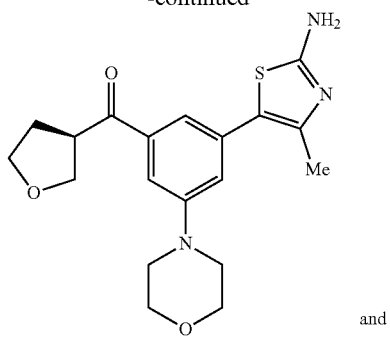
and
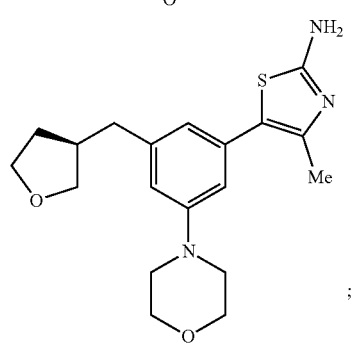
;
or a pharmaceutically acceptable salt thereof.
Also provided are compounds selected from the group consisting of:
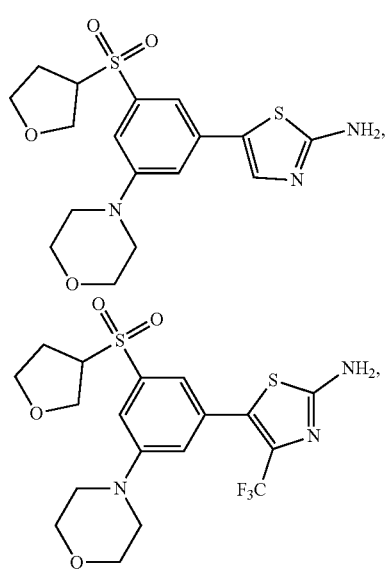
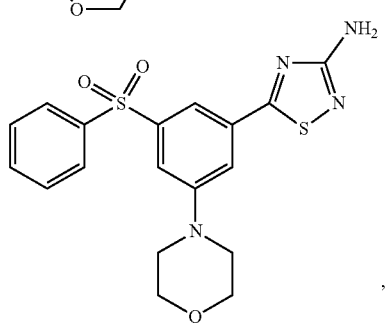
,
-continued
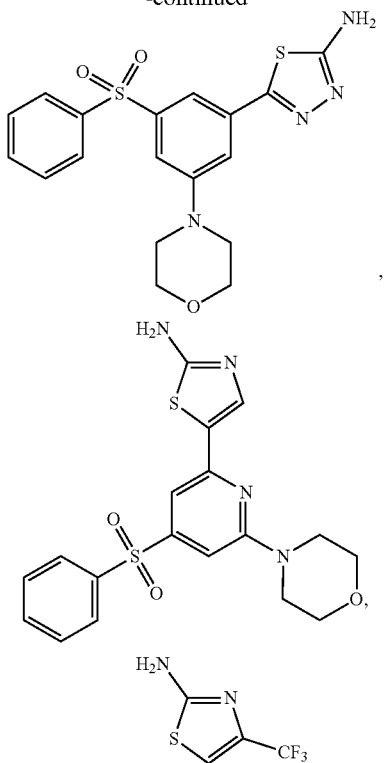
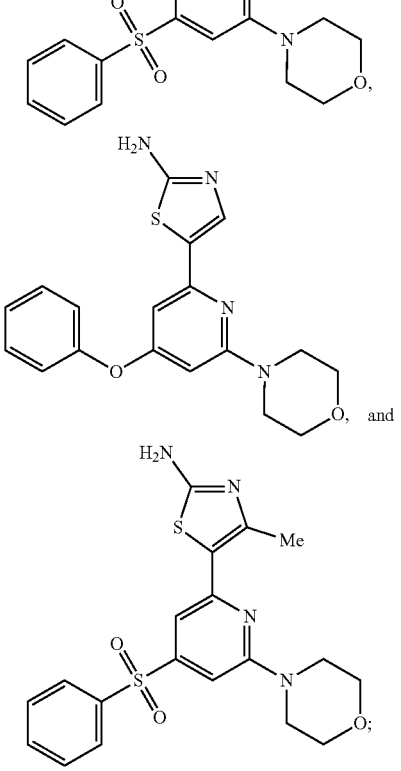
or a pharmaceutically acceptable salt thereof.
In some embodiments, the compound is selected from the group consisting of:

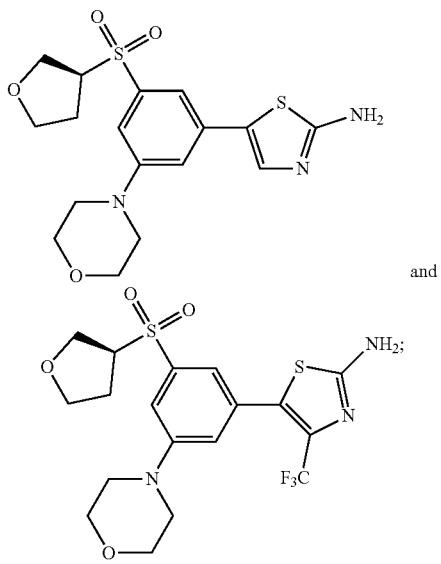

or a pharmaceutically acceptable salt thereof.

Also provided are pharmaceutical compositions comprising (a) at least one compound of Formula (I), or a pharmaceutically acceptable salt thereof, and (b) a pharmaceutically acceptable excipient.

Provided in other aspects are methods of treating a disease or medical condition associated with regulation of the Vps34/PI3K III signaling pathway, comprising administering to a subject in need of such treatment an effective amount of at least one compound of Formula (I), or a pharmaceutically acceptable salt thereof, or a pharmaceutical composition comprising a compound of Formula (I). In some embodiments, the disease or medical condition is diabetes, polycystic ovarian syndrome, diabetes-associated cardiovascular disease, cancer, neuro-inflammation or ischemic stroke. In some embodiments of the methods provided herein, the disease or medical condition is cancer, and the cancer is glioblastoma, renal cell carcinoma, or melanoma.

In some aspects, any compound of Formula (I), or a pharmaceutically acceptable salt thereof, or a pharmaceutical composition comprising a compound of Formula (I), is used in the treatment of a disease or medical condition associated with regulation of the Vps34/PI3K III signaling pathway. In some embodiments, the disease or medical condition is diabetes, polycystic ovarian syndrome, diabetes-associated cardiovascular disease, cancer, neuro-inflammation or ischemic stroke. In some embodiments of the uses provided herein, the disease or medical condition is cancer, and the cancer is glioblastoma, renal cell carcinoma, or melanoma.

Also provided is the use of at least one compound of Formula (I), or a pharmaceutically acceptable salt thereof, or a pharmaceutical composition containing at least one compound of Formula (I), in the manufacture of a medicament for the treatment of a disease or medical condition associated with regulation of the Vps34/PI3K III signaling pathway. In some embodiments, the disease or medical condition is diabetes, polycystic ovarian syndrome, diabetes-associated cardiovascular disease, cancer, neuro-inflammation or ischemic stroke. In some embodiments of the uses provided herein, the disease or medical condition is cancer, and the cancer is glioblastoma, renal cell carcinoma, or melanoma.

In yet another aspect, provided are methods of interfering with the Vps34/PI3K III signaling pathway in a cell, or modulating, preventing, slowing, reversing, or inhibiting of the Vps34/PI3K III signaling pathway in a cell, comprising contacting the cell with an effective amount of at least one compound of Formula (I), or a salt thereof, and/or with at least one pharmaceutical composition comprising a compound of Formula (I), wherein the contacting is in vitro, ex vivo, or in vivo.

DETAILED DESCRIPTION

The present disclosure relates to thiazole- or diathiazole-substituted aryl and heteroaryl compounds, pharmaceutical compositions containing them, and methods of using them, including treatment of disorders or disease related to regulation of the Vps34/PI3K III signaling pathway.

It is to be understood that this disclosure is not limited to particular embodiments described, as such may, of course, vary. It is also to be understood that the terminology used herein is for the purpose of describing particular embodiments only, and is not intended to be limiting.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4th edition, New York: Oxford University Press, 2002, pp. 360-361, 1084-1085; Smith and March, March's Advanced Organic Chemistry: Reactions, Mechanisms, and Structure, 5th edition, Wiley-Interscience, 2001.

The nomenclature used herein to name the subject compounds is illustrated in the Examples herein. This nomenclature has generally been derived using the commercially-available ChemBioDraw Ultra software, Version 14.0.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Terms

The following terms have the following meanings unless otherwise indicated. Any undefined terms have their art recognized meanings.

The term "alkyl" refers to a straight- or branched-chain univalent saturated hydrocarbon group, or combination thereof, having the number of carbon atoms designated (i.e., $C_1$-$C_{10}$ means one to ten carbon atoms). Examples of alkyl groups include, but are not limited to, groups such as methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. In some instances, alkyl groups are $C_{1-4}$alkyl.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Haloalkyl" refers to an alkyl group as described above, wherein one or more hydrogen atoms on the alkyl group have been replaced with a halo group. Examples of such groups include, without limitation, fluoroalkyl groups, such as fluoroethyl, trifluoromethyl, difluoromethyl, trifluoroethyl, and the like.

"Aryl" or "Ar" refers to a monovalent aromatic carbocyclic group of from 6 to 18 annular carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl.

"Cycloalkyl" refers to cyclic hydrocarbon groups of from 3 to 10 annular carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like. In some instances, the cycloalkyl is a monocyclic ring. In some instances, cycloalkyl is a 3- to 6-membered ring.

"Cycloalkenyl" refers to non-aromatic cyclic hydrocarbon groups of from 3 to 10 annular carbon atoms having single or multiple cyclic rings and having at least one >C=C<ring unsaturation. In some embodiments, the cycloalkenyl has 1 or 2 sites of >C=C<ring unsaturation. Examples of cycloalkenyl groups include cyclopropenyl, cyclobutenyl, cyclopentenyl, cyclohexenyl and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 5 to 12 ring atoms per heterocycle. Such heteroaryl groups comprise at least one ring within the ring system that is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. In some instances, heteroaryl groups are 5-, 6-, 8-, 9-, or 10-membered ring systems.

Examples of heteroaryls include, but are not limited to, pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, benzofuran, benzothiophene, indazole, benzimidazole, benzothiazole, benzoxazole, indolizine, isoindole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, phenoxazine, phenothiazine, phthalimide, and the like.

"Heterocycloalkyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —$SO_2$— moieties. Examples of heterocycloalkyls include, but are not limited to, azetidine, oxetane, tetrahydrofuran, pyrrolidine, piperazine, piperidine, morpholine, thiomorpholine, 1,1-dioxothiomorpholinyl, dihydroindole, indazole, quinolizine, imidazolidine, imidazoline, indoline, 1,2,3,4-tetrahydroisoquinoline, thiazoline, and the like. In some instances, heterocycloalkyl groups are 4-, 5-, or 6-membered rings. In some instances, the heterocycloalkyl comprises a fused phenyl ring.

"Halo" or "halogen" refers to fluoro, chloro, bromo, and iodo.

In addition to the disclosure herein, the term "substituted," when used to modify a specified group or radical, can also mean that one or more hydrogen atoms of the specified group or radical are each, independently of one another, replaced with the same or different substituent groups as defined below. Substituent groups include, but are not limited to, alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of the present disclosure and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of the present disclosure for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The present disclosure also includes pharmaceutically acceptable salts of the compounds represented by Formula (I), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Particular pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methyl sulfonates, propyl sulfonates, besylates, xylenesulfonates, naphthalene-1-sulfonates, naphthalene-2-sulfonates, phenyl acetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (I) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenyl acetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethyl sulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Compounds

Compounds and salts thereof (such as pharmaceutically acceptable salts) are detailed herein, including in the Summary and in the appended claims. Also provided are the use of all of the compounds described herein, including salts and solvates of the compounds described herein, as well as methods of making such compounds. Any compound described herein may also be referred to as a drug.

In one aspect, provided are compounds of Formula (I):

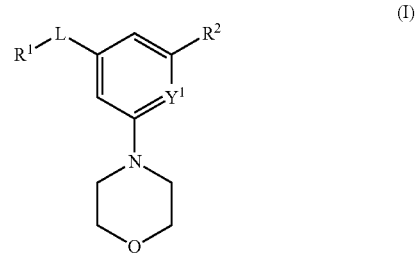

wherein
$R^1$ is $C_6$-$C_{14}$ aryl, 5- to 10-membered heteroaryl, $C_3$-$C_6$ cycloalkyl, or 4- to 10-membered heterocycloalkyl, wherein the $C_6$-$C_{14}$ aryl, 5- to 10-membered heteroaryl, $C_3$-$C_6$ cycloalkyl, or 4- to 10-membered heterocycloalkyl of $R^1$ are each unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl;

L is —S(O)$_2$—, —O—, —C(O)— or —CH$_2$—;
$Y^1$ is CH or N; and
$R^2$ is a 5-membered heteroaryl or a 5-membered heterocycloalkyl, wherein the 5-membered heteroaryl and 5-membered heterocycloalkyl of $R^2$ are each unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl;

$R^a$, $R^b$, $R^c$, $R^d$, $R^e$, and $R^f$ are each independently H or $C_{1-4}$ alkyl;

wherein when L is —S(O)$_2$— and $Y^1$ is N, $R^1$ is not 4,4-difluoro-piperidin1-yl;

or a pharmaceutically acceptable salt thereof.

In some embodiments of Formula (I), $R^1$ is $C_6$-$C_{14}$ aryl, 5- to 10-membered heteroaryl, $C_3$-$C_6$ cycloalkyl, or 4- to 10-membered heterocycloalkyl, each substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, and —NR$^a$C(O)OR$^b$. In some embodiments of Formula (I), $R^1$ is $C_6$-$C_{14}$ aryl, 5- to 10-membered heteroaryl, $C_3$-$C_6$ cycloalkyl, or 4- to 10-membered heterocycloalkyl, wherein the $C_6$-$C_{14}$ aryl, 5- to 10-membered heteroaryl, $C_3$-$C_6$ cycloalkyl, or 4- to 10-membered heterocycloalkyl of $R^1$ are each unsubstituted or substituted with one or more substituents selected from the group consisting of halogen, —CN, —NO$_2$, C$_1$-C$_6$ alkyl, C$_1$-C$_6$ haloalkyl, C$_2$-C$_6$ alkenyl, C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, and —NR$^a$C(O)OR$^b$. In some embodiments of Formula (I), R$^1$ is C$_6$-C$_{14}$ aryl, 5- to 10-membered heteroaryl, C$_3$-C$_6$ cycloalkyl, or 4- to 10-membered heterocycloalkyl, wherein the C$_6$-C$_{14}$ aryl, 5- to 10-membered heteroaryl, C$_3$-C$_6$ cycloalkyl, or 4- to 10-membered heterocycloalkyl of R$^1$ are each unsubstituted or substituted with one or more substituents selected from the group consisting of C$_1$-C$_6$ alkyl, C$_1$-C$_6$ haloalkyl, and —NR$^b$R$^c$. In some embodiments of Formula (I), R$^1$ is C$_6$-C$_{14}$ aryl, 5- to 10-membered heteroaryl, C$_3$-C$_6$ cycloalkyl, or 4- to 10-membered heterocycloalkyl, each unsubstituted.

In some embodiments of Formula (I), R$^1$ is C$_6$ or C$_{10}$ aryl, 5- to 6-membered heteroaryl, C$_5$-C$_6$ cycloalkyl, or 5- to 6-membered heterocycloalkyl, each substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, and —NR$^a$C(O)OR$^b$. In some embodiments of Formula (I), R$^1$ is C$_6$ or C$_{10}$ aryl, 5- to 6-membered heteroaryl, C$_5$-C$_6$ cycloalkyl, or 5- to 6-membered heterocycloalkyl, wherein the C$_6$ or C$_{10}$ aryl, 5- to 6-membered heteroaryl, C$_5$-C$_6$ cycloalkyl, or 5- to 6-membered heterocycloalkyl of R$^1$ are each unsubstituted or substituted with one or more substituents selected from the group consisting of halogen, —CN, —NO$_2$, C$_1$-C$_6$ alkyl, C$_1$-C$_6$ haloalkyl, C$_2$-C$_6$ alkenyl, C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, and —NR$^a$C(O)OR$^b$. In some embodiments of Formula (I), R$^1$ is C$_6$ or C$_{10}$ aryl, 5- to 6-membered heteroaryl, C$_5$-C$_6$ cycloalkyl, or 5- to 6-membered heterocycloalkyl, wherein the C$_6$ or C$_{10}$ aryl, 5- to 6-membered heteroaryl, C$_5$-C$_6$ cycloalkyl, or 5- to 6-membered heterocycloalkyl of R$^1$ are each unsubstituted or substituted with one or more substituents selected from the group consisting of C$_1$-C$_6$ alkyl, C$_1$-C$_6$ haloalkyl, and —NR$^b$R$^c$. In some embodiments of Formula (I), R$^1$ is C$_6$ or C$_{10}$ aryl, 5- to 6-membered heteroaryl, C$_5$-C$_6$ cycloalkyl, or 5- to 6-membered heterocycloalkyl, each unsubstituted.

In some embodiments of Formula (I), R$^1$ is a C$_6$-C$_{14}$ aryl, unsubstituted or substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted C$_3$-C$_6$ cycloalkyl, substituted or unsubstituted C$_3$-C$_6$ cycloalkenyl, substituted or unsubstituted C$_6$-C$_{14}$ aryl, substituted or unsubstituted 5- to 10-membered heteroaryl, and substituted or unsubstituted 4- to 10-membered heterocycloalkyl. In some embodiments, R$^1$ is phenyl or naphthyl, substituted with one or more substituents selected from the group consisting of halogen, —CN, —NO$_2$, C$_1$-C$_6$ alkyl, C$_2$-C$_6$ alkenyl, C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, C$_3$-C$_6$ cycloalkyl, C$_3$-C$_6$ cycloalkenyl, C$_6$-C$_{14}$ aryl, 5- to 10-membered heteroaryl, and 4- to 10-membered heterocycloalkyl. In some embodiments, R$^1$ is phenyl. In some embodiments, R$^1$ is naphthyl.

In some embodiments, R$^1$ is a 4- to 10-membered heterocycloalkyl, unsubstituted or substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted C$_3$-C$_6$ cycloalkyl, substituted or unsubstituted C$_3$-C$_6$ cycloalkenyl, substituted or unsubstituted C$_6$-C$_{14}$ aryl, substituted or unsubstituted 5- to 10-membered heteroaryl, and substituted or unsubstituted 4- to 10-membered heterocycloalkyl. In other embodiments, R$^1$ is a 5- to 6-membered heterocycloalkyl, substituted with one or more substituents selected from the group consisting of halogen, —CN, —NO$_2$, C$_1$-C$_6$ alkyl, C$_2$-C$_6$ alkenyl, C$_2$-C$_6$ alkynyl, C$_3$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, C$_3$-C$_6$ cycloalkyl, C$_3$-C$_6$ cycloalkenyl, C$_6$-C$_{14}$ aryl, 5- to 10-membered heteroaryl, and 4- to 10-membered heterocycloalkyl. In some embodiments, R$^1$ is oxetanyl, azetidinyl, tetrahydrofuranyl, pyrrolidinyl, tetrahydropyranyl, piperidinyl, piperazinyl, morpholinyl, thiomorpholinyl, 1,1-dioxothiomorpholinyl, azepinyl, or diazepinyl, each unsubstituted or substituted with one or more substituents selected from the group consisting of halogen, —CN, —NO$_2$, C$_1$-C$_6$ alkyl, C$_2$-C$_6$ alkenyl, C$_2$-C$_6$ alkynyl, C$_3$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, C$_3$-C$_6$ cycloalkyl, C$_3$-C$_6$ cycloalkenyl, C$_6$-C$_{14}$ aryl, 5- to 10-membered heteroaryl, and 4- to 10-membered heterocycloalkyl. In some embodiments, R$^1$ is tetrahydrofuranyl, tetrahydropyranyl, pyrrolidinyl, piperidinyl, piperazinyl, or morpholinyl, each unsubstituted or substituted with one or more substituents selected from the group consisting of C$_1$-C$_6$ alkyl, C$_1$-C$_6$ haloalkyl, and —NR$^b$R$^c$, wherein R$^b$ and R$^c$ are each independently H or C$_{1-4}$ alkyl. In some embodiments, R$^1$ is unsubstituted tetrahydrofuranyl. In some embodiments, R$^1$ is tetrahydrofuranyl substituted with one or more substituents selected from the group consisting of C$_1$-C$_6$ alkyl, C$_1$-C$_6$ haloalkyl, —NHC$_{1-4}$ alkyl, —N(C$_{1-4}$ alkyl)$_2$, and NH$_2$. In some embodiments, R$^1$ is unsubstituted tetrahydropyranyl. In some embodiments, R$^1$ is tetrahydropyranyl substituted with one or more substituents selected from the group consisting of C$_1$-C$_6$ alkyl, C$_1$-C$_6$ haloalkyl, —NHC$_{1-4}$ alkyl, —N(C$_{1-4}$ alkyl)$_2$, and NH$_2$. In certain embodiments, R$^1$ is tetrahydrofuran-3-yl. In other embodiments, R$^1$ is tetrahydropyran-4-yl. In some embodiments, R$^1$ is unsubstituted piperidine. In some embodiments, when Y$^1$ is N, R$^1$ is unsubstituted piperidine.

In some embodiments, L is —S(O)$_2$—. In some embodiments, L is —O—. In some embodiments, L is —C(O)—. In some embodiments, L is —CH$_2$—.

In some embodiments, Y$^1$ is CH. In some embodiments, Y$^1$ is N.

In some embodiments of Formula (I), R$^2$ is a 5-membered heteroaryl or a 5-membered heterocycloalkyl, each of which is optionally substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)

NR$^e$R$^f$, —OC(O)NR$^e$R$^f$, —NR$^d$C(O)R$^e$, and —NR$^d$C(O)OR$^e$. In some embodiments, R$^2$ is a 5-membered heteroaryl or a 5-membered heterocycloalkyl, each of which is optionally substituted with one or more substituents selected from the group consisting of C$_{1-6}$ alkyl, C$_{1-6}$ haloalkyl and NR$^e$R$^f$.

In some embodiments of Formula (I), R$^2$ is a 5-membered heteroaryl ring; substituted with one or more substituents selected from C$_{1-6}$ alkyl, C$_{1-6}$ haloalkyl and NR$^e$R$^f$; wherein R$^e$ and R$^f$ are independently H or C$_{1-4}$ alkyl. In some embodiments, R$^2$ is a 5-membered heteroaryl ring substituted with one or more substituents selected from C$_{1-6}$ alkyl, C$_{1-6}$ haloalkyl, NHC$_{1-4}$alkyl, N(C$_{1-4}$alkyl)$_2$, and NH$_2$. In some embodiments, R$^2$ is a 5-membered heteroaryl ring substituted with one or more substituents selected from the group consisting of methyl, ethyl, propyl, iso-propyl, butyl, sec-butyl, iso-butyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, NHCH$_3$, NH$_2$. In other embodiments, R$^2$ is a 5-membered heteroaryl ring substituted with NR$^e$R$^f$; wherein R$^e$ and R$^f$ are independently hydrogen or methyl. In other embodiments, R$^2$ is a 5-membered heteroaryl ring substituted with NH$_2$. In some embodiments, R$^2$ is a 5-membered heteroaryl ring substituted with C$_{1-6}$haloalkyl. In some embodiments, R$^2$ is a 5-membered heteroaryl ring substituted with trifluoromethyl or difluoroethyl. In some embodiments, R$^2$ is a 5-membered heteroaryl ring substituted with trifluoromethyl. In some embodiments, R$^2$ is a 5-membered heteroaryl ring substituted with C$_{1-6}$ alkyl. In some embodiments, R$^2$ is a 5-membered heteroaryl ring; substituted with C$_{1-6}$ alkyl and NR$^e$R$^f$; wherein R$^e$ and R$^f$ are both H. In some embodiments, R$^2$ is a 5-membered heteroaryl ring; substituted with C$_{1-6}$ haloalkyl and NR$^e$R$^f$; wherein R$^e$ and R$^f$ are both H. In some embodiments, the R$^2$ is a 5-membered heteroaryl ring that includes one, two, or three heteroatoms selected from the group consisting of N, S, and O. In some embodiments, the R$^2$ is a 5-membered heteroaryl ring that includes one or two nitrogen ring members. In some embodiments, the R$^2$ is a 5-membered heteroaryl ring that includes a sulfur atom. In some embodiments, R$^2$ is a 5-membered heteroaryl that includes one nitrogen ring member. In some embodiments, R$^2$ is selected from the group consisting of pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, isoindolyl, benzofuranyl, benzothiophenyl, benzimidazolyl, benzothiazolyl, or benzoxazolyl, each optionally substituted with one or more substituents selected from C$_{1-6}$ alkyl, C$_{1-6}$ haloalkyl and NR$^e$R$^f$. In some embodiments, R$^2$ is thiazole or thiadiazole, each optionally substituted with one or more substituents selected from C$_{1-6}$ alkyl, C$_{1-6}$ haloalkyl and NR$^e$R$^f$. In some embodiments, R$^2$ is thiazolyl or thiadiazolyl substituted with one or more substituents elected from methyl, CF$_3$ and NH$_2$. In some embodiments, R$^2$ is thiazolyl substituted with one or more substituents selected from C$_{1-6}$ alkyl, C$_{1-6}$ haloalkyl and NR$^e$R$^f$. In some embodiments, R$^2$ is 1,3-thiazole substituted with one or more substituents selected from methyl, CF$_3$ and NH$_2$. In some embodiments, R$^2$ is thiadiazolyl substituted with one or more substituents selected from C$_{1-6}$ alkyl, C$_{1-6}$ haloalkyl and NR$^e$R$^f$. In some embodiments, R$^2$ is 1,2,3-thiadiazole, 1,2,4-thiadiazole, 1,2,5-thiadiazole, or 1,3,4-thiadiazole, each optionally substituted with one or more substituents selected from C$_{1-6}$ alkyl, C$_{1-6}$ haloalkyl and NR$^e$R$^f$. In some embodiments, R$^2$ is 1,3,4-thiadiazole, substituted with one or more substituents selected from methyl, CF$_3$ and NH$_2$.

In some embodiments, R$^2$ is

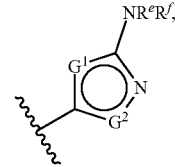

wherein G$^1$ is S or N; G$^2$ is CR$^3$, S, or N; R$^3$ is H, C$_{1-6}$ alkyl or C$_{1-6}$ haloalkyl; and R$^e$ and R$^f$ are independently H or C$_{1-4}$ alkyl. In some embodiments, G$^1$ is S. In some embodiments, G$^1$ is N. In some embodiments, G$^2$ is CR$^3$, wherein R$^3$ is C$_{1-6}$ alkyl or C$_{1-6}$ haloalkyl. In some embodiments, G$^2$ is CH. In other embodiments, G$^2$ is CR$^3$, wherein R$^3$ is C$_{1-6}$ alkyl. In other embodiments, G$^2$ is CR$^3$, wherein R$^3$ is C$_{1-6}$ haloalkyl. In some embodiments, G$^2$ is S. In some embodiments, G$^2$ is N.

In some embodiments, R$^2$ is

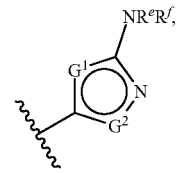

wherein one of R$^e$ and R$^f$ is H and the other is C$_{1-4}$ alkyl. In some embodiments, R$^e$ and R$^f$ are both C$_{1-4}$ alkyl. In some embodiments, R$^e$ and R$^f$ are both 11.

In some embodiments, R$^2$ is

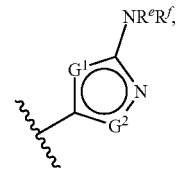

wherein G$^1$ is S, G$^2$ is CR$^3$, S, or N; wherein R$^3$ is H, C$_{1-6}$ alkyl or C$_{1-6}$ haloalkyl, and R$^a$ and R$^b$ are both H. In some embodiments, G$^1$ is N, G$^2$ is CR$^3$, S, or N; wherein R$^3$ is H, C$_{1-6}$ alkyl or C$_{1-6}$ haloalkyl, and R$^a$ and R$^b$ are both H. In some embodiments, R$^2$ is

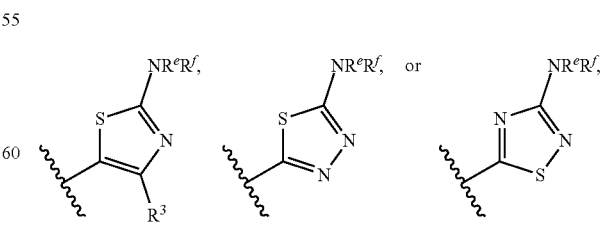

wherein R$^3$ is H, C$_{1-6}$ alkyl or C$_{1-6}$ haloalkyl, and R$^e$ and R$^f$ are independently H or C$_{1-4}$ alkyl. In some embodiments, R$^2$ is

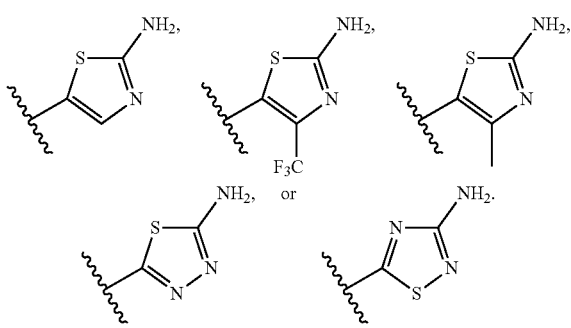

In some embodiments, $R^2$ is

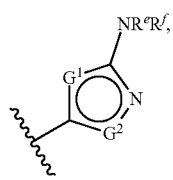

wherein $G^1$ is S or N, $G^2$ is $CR^3$; $R^3$ is H, $C_{1-6}$ alkyl or $C_{1-6}$ haloalkyl, and $R^e$ and $R^f$ are both H. In some embodiments, $G^1$ is S or N, $G^2$ is S, and $R^e$ and $R^f$ are each independently H or $C_{1-4}$ alkyl. In some embodiments, $G^1$ is S or N, $G^2$ is N, and $R^e$ and $R^f$ are each independently H or $C_{1-4}$ alkyl.

In some embodiments, $R^2$ is

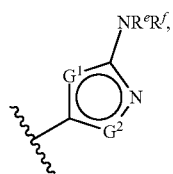

wherein $G^1$ is S or N, $G^2$ is $CR^3$; $R^3$ is H, and $R^a$ and $R^b$ are each independently H or $C_{1-4}$ alkyl. In some embodiments, $G^1$ is S or N, $G^2$ is $CR^3$; wherein $R^3$ is $C_{1-6}$ alkyl, and $R^e$ and $R^f$ are each independently H or $C_{1-4}$ alkyl. In some embodiments, $G^1$ is S or N, $G^2$ is $CR^3$; wherein $R^3$ is $C_{1-6}$ haloalkyl, and $R^e$ and $R^f$ are each independently H or $C_{1-4}$ alkyl.

In some embodiments of Formula (I), $R^1$ is $C_6$-$C_{14}$ aryl and $R^2$ is a 5-membered heteroaryl, wherein $R^1$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a 5- to 10-membered heteroaryl and $R^2$ is a 5-membered heteroaryl, wherein $R^1$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a $C_3$-$C_6$ cycloalkyl, and $R^2$ is a 5-membered heteroaryl, wherein $R^1$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a 4- to 10-membered heterocycloalkyl, and $R^2$ is a 5-membered heteroaryl, wherein $R^1$ is unsubstituted or substituted with one or more substituents selected from the group consisting of halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_3$-$C_6$ haloalkyl, —$OR^d$, —$SR^d$, —$S(O)_2R^d$, —$NR^eR^f$, —$C(O)R^d$, —$OC(O)R^d$, —$C(O)OR^d$, —$C(O)NR^eR^f$, —$OC(O)NR^eR^f$, —$NR^dC(O)R^e$, —$NR^dC(O)OR^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments of Formula (I), $R^1$ is $C_6$-$C_{14}$ aryl and $R^2$ is a 5-membered heterocycloalkyl, wherein $R^1$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^a$, —$SR^a$, —$S(O)_2R^a$, —$NR^bR^c$, —$C(O)R^a$, —$OC(O)R^a$, —$C(O)OR^a$, —$C(O)NR^bR^c$, —$OC(O)NR^bR^c$, —$NR^aC(O)R^b$, —$NR^aC(O)OR^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^d$, —$SR^d$, —$S(O)_2R^d$, —$NR^eR^f$, —$C(O)R^d$, —$OC(O)R^d$, —$C(O)OR^d$, —$C(O)NR^eR^f$, —$OC(O)NR^eR^f$, —$NR^dC(O)R^e$, —$NR^dC(O)OR^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a 5- to 10-membered heteroaryl and $R^2$ is a 5-membered heterocycloalkyl, wherein $R^1$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^a$, —$SR^a$, —$S(O)_2R^a$, —$NR^bR^c$, —$C(O)R^a$, —$OC(O)R^a$, —$C(O)OR^a$, —$C(O)NR^bR^c$, —$OC(O)NR^bR^c$, —$NR^aC(O)R^b$, —$NR^aC(O)OR^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_3$-$C_6$ haloalkyl, —$OR^d$, —$SR^d$, —$S(O)_2R^d$, —$NR^eR^f$, —$C(O)R^d$, —$OC(O)R^d$, —$C(O)OR^d$, —$C(O)NR^eR^f$, —$OC(O)NR^eR^f$, —$NR^dC(O)R^e$, —$NR^dC(O)OR^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a $C_3$-$C_6$ cycloalkyl, and $R^2$ is a 5-membered heterocycloalkyl, wherein $R^1$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^a$, —$SR^a$, —$S(O)_2R^a$, —$NR^bR^c$, —$C(O)R^a$, —$OC(O)R^a$, —$C(O)OR^a$, —$C(O)NR^bR^c$, —$OC(O)NR^bR^c$, —$NR^aC(O)R^b$, —$NR^aC(O)OR^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^d$, —$SR^d$, —$S(O)_2R^d$, —$NR^eR^f$, —$C(O)R^d$, —$OC(O)R^d$, —$C(O)OR^d$, —$C(O)NR^eR^f$, —$OC(O)NR^eR^f$, —$NR^dC(O)R^e$, —$NR^dC(O)OR^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is a 4- to 10-membered heterocycloalkyl, and $R^2$ is a 5-membered heterocycloalkyl, wherein $R^1$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_1$-$C_6$ haloalkyl, —$OR^a$, —$SR^a$, —$S(O)_2R^a$, —$NR^bR^c$, —$C(O)R^a$, —$OC(O)R^a$, —$C(O)OR^a$, —$C(O)NR^bR^c$, —$OC(O)NR^bR^c$, —$NR^aC(O)R^b$, —$NR^aC(O)OR^b$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl, and $R^2$ is unsubstituted or substituted with one or more substituents selected from the group consisting of halogen, —CN, —$NO_2$, substituted or unsubstituted $C_1$-$C_6$ alkyl, substituted or unsubstituted $C_2$-$C_6$ alkenyl, substituted or unsubstituted $C_2$-$C_6$ alkynyl, $C_3$-$C_6$ haloalkyl, —$OR^d$, —$SR^d$, —$S(O)_2R^d$, —$NR^eR^f$, —$C(O)R^d$, —$OC(O)R^d$, —$C(O)OR^d$, —$C(O)NR^eR^f$, —$OC(O)NR^eR^f$, —$NR^dC(O)R^e$, —$NR^dC(O)OR^e$, substituted or unsubstituted $C_3$-$C_6$ cycloalkyl, substituted or unsubstituted $C_3$-$C_6$ cycloalkenyl, substituted or unsubstituted $C_6$-$C_{14}$ aryl, substituted or unsubstituted 5- to 10-membered heteroaryl, and substituted or unsubstituted 4- to 10-membered heterocycloalkyl.

In some embodiments, $R^1$ is $C_6$-$C_{14}$ aryl, L is —$S(O)_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —O—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —C(O)—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —$CH_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is phenyl or napthyl, L is —$S(O)_2$—, $Y^1$ is CH, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —O—, $Y^1$ is CH, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —C(O)—, $Y^1$ is CH, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —$CH_2$—, $Y^1$ is CH, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is $C_6$-$C_{14}$ aryl, L is —$S(O)_2$—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —O—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —C(O)—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is $C_6$-$C_{14}$ aryl, L is —$CH_2$—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is phenyl or napthyl, L is —$S(O)_2$—, $Y^1$ is N, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —O—, $Y^1$ is N, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —C(O)—, $Y^1$ is N, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is phenyl or napthyl, L is —$CH_2$—, $Y^1$ is N, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is a 5- or 6-membered heterocycloalkyl, L is —$S(O)_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —O—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —C(O)—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —$CH_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is tetrahydrofuranyl, tetrahydropyranyl, pyrrolidinyl, piperidinyl, piperazinyl, or morpholinyl, L is —$S(O)_2$—, $Y^1$ is CH, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —O—, $Y^1$ is CH, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —C(O)—, $Y^1$ is CH, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —$CH_2$—, $Y^1$ is CH, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is a 5- or 6-membered heterocycloalkyl, L is —$S(O)_2$—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —O—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —C(O)—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is a 5- or 6-membered heterocycloalkyl L is —$CH_2$—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is tetrahydrofuranyl, tetrahydropyranyl, pyrrolidinyl, piperidinyl, piperazinyl, or morpholinyl, L is —$S(O)_2$—, $Y^1$ is N, and $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —O—, $Y^1$ is N, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —C(O)—, $Y^1$ is N, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, tetrahydropyranyl, pyrrolidinyl, piperidinyl, piperazinyl, or morpholinyl, L is —CH$_2$—, $Y^1$ is N, $R^2$ is thiazolyl or thiadiazolyl; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is tetrahydrofuranyl, L is —S(O)$_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —O—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —C(O)—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —CH$_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —S(O)$_2$—, $Y^1$ is N, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —O—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —C(O)—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydrofuranyl, L is —CH$_2$—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is tetrahydropyranyl, L is —S(O)$_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —O—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —C(O)—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —CH$_2$—, $Y^1$ is CH, and $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —S(O)$_2$—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —O—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —C(O)—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl. In some embodiments, $R^1$ is tetrahydropyranyl, L is —CH$_2$—, $Y^1$ is N, $R^2$ is a 5-membered heteroaryl ring; substituted with one or more substituents selected from $C_{1-6}$ alkyl, $C_{1-6}$ haloalkyl and $NR^aR^b$; wherein $R^a$ and $R^b$ are independently H or $C_{1-4}$ alkyl.

In some embodiments, $R^1$ is phenyl or napthyl, L is —S(O)$_2$—, $Y^1$ is CH, and $R^2$ is

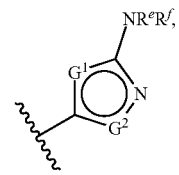

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —O—, $Y^1$ is CH, and $R^2$ is

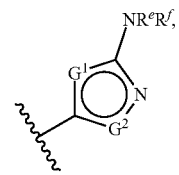

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —C(O)—, $Y^1$ is CH, and $R^2$ is

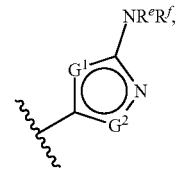

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —CH$_2$—, $Y^1$ is CH, and $R^2$ is

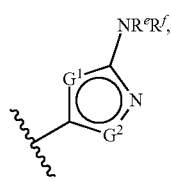

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —S(O)$_2$—, $Y^1$ is N, and $R^2$ is

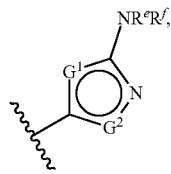

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —O—, $Y^1$ is N, and $R^2$ is

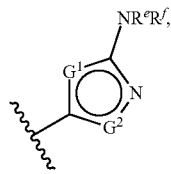

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —C(O)—, $Y^1$ is N, and $R^2$ is

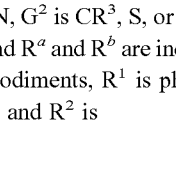

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is phenyl or napthyl, L is —CH$_2$—, $Y^1$ is N, and $R^2$ is

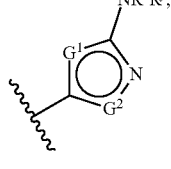

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl.

In some embodiments, $R^1$ is a 5- or 6-membered heterocycloalkyl, L is —S(O)$_2$—, $Y^1$ is CH, and $R^2$ is

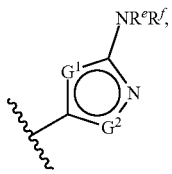

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —O—, $Y^1$ is CH, and $R^2$ is

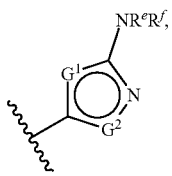

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —C(O)—, $Y^1$ is CH, and $R^2$ is

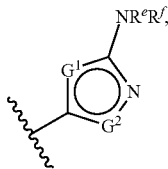

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —CH$_2$—, $Y^1$ is CH, and $R^2$ is

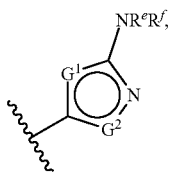

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —S(O)$_2$—, $Y^1$ is N, and $R^2$ is

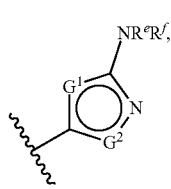

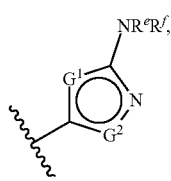

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —O—, $Y^1$ is N, and $R^2$ is

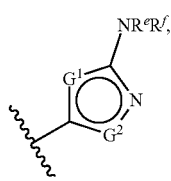

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —C(O)—, $Y^1$ is N, and $R^2$ is

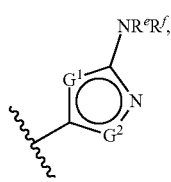

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl. In some embodiments, $R^1$ is a 5- or 6-membered heterocycloalkyl, L is —$CH_2$—, $Y^1$ is N, and $R^2$ is

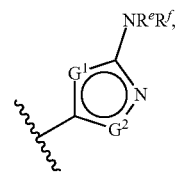

wherein $G^1$ is S or N, $G^2$ is $CR^3$, S, or N, $R^3$ is H, $C_{1-6}$ alkyl or $C_{1-6}$ haloalkyl, and $R^a$ and $R^b$ are independently H or $C_{1-4}$ alkyl.

In some embodiments of Formula (I), $R^1$ is $C_6$-$C_{14}$ aryl or 4- to 10-membered heterocycloalkyl;

L is —$S(O)_2$— or —O—;

$Y^1$ is CH or N; and $R^2$ is a 5-membered heteroaryl ring; substituted with one or more substituents selected from the group consisting of $C_{1-6}$ alkyl, $C_{1-6}$ haloalkyl and $NR^eR^f$;

$R^e$ and $R^f$ are independently H or $C_{1-4}$ alkyl;

or a pharmaceutically acceptable salt thereof.

Any variation or embodiment of $R^1$, $R^2$, Yi, $R^a$, $R^b$, $R^c$, $R^d$, $R^e$, $R^f$, L, $G^1$, $G^2$, and $R^3$ provided herein can be combined with every other variation or embodiment of $R^1$, $R^2$, Yi, $R^a$, $R^b$, $R^c$, $R^d$, $R^e$, $R^f$, L, $G^1$, $G^2$, and $R^3$, as if each combination had been individually and specifically described.

In other embodiments, the compound of Formula (I) is selected from the group consisting of compounds of Table 1:

TABLE 1

| Ex. # | Structure | Chemical Name |
|---|---|---|
| 1 | 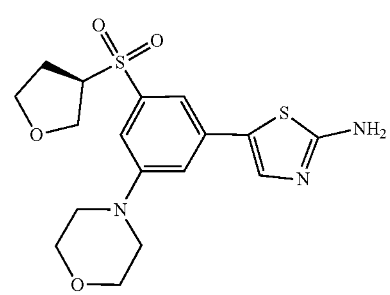 [SMILES: Nc1ncc(-c2cc(N3CCOCC3)cc(S(=O)(=O)[C@@H]3CCOC3)c2)s1] | (R)-5-(3-morpholino-5-((tetrahydrofuran-3-yl)sulfonyl)phenyl)thiazol-2-amine |
| 2 | 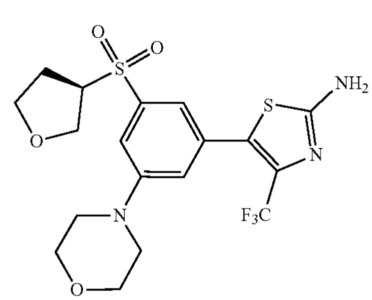 [SMILES: Nc1nc(C(F)(F)F)c(-c2cc(N3CCOCC3)cc(S(=O)(=O)[C@@H]3CCOC3)c2)s1] | (R)-5-(3-morpholino-5-((tetrahydrofuran-3-yl)sulfonyl)phenyl)-4-(trifluoromethyl)thiazol-2-amine |

TABLE 1-continued
| Ex. # | Structure | Chemical Name |
|---|---|---|
| 3 | 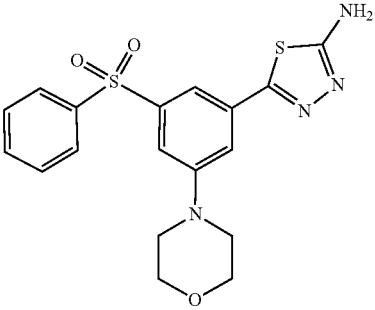 | 5-(3-morpholino-5-(phenylsulfonyl)phenyl)-1,3,4-thiadiazol-2-amine |
| 4 | 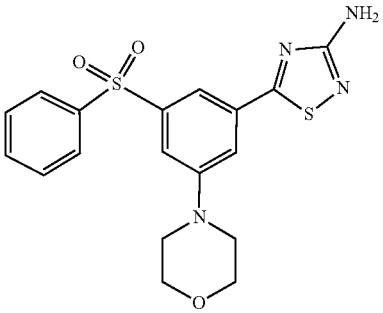 | 5-(3-morpholino-5-(phenylsulfonyl)phenyl)-1,2,4-thiadiazol-3-amine |
| 5 | 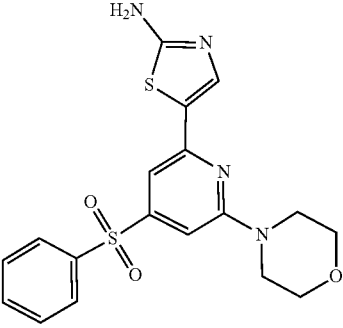 [SMILES: Nc1ncc(-c2cc(S(=O)(=O)c3ccccc3)cc(N3CCOCC3)n2)s1] | 5-(6-morpholino-4-(phenylsulfonyl)pyridin-2-yl)thiazol-2-amine |
| 6 | 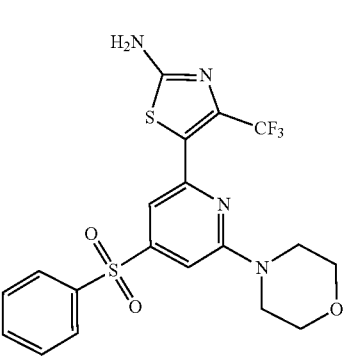 [SMILES: Nc1nc(C(F)(F)F)c(-c2cc(S(=O)(=O)c3ccccc3)cc(N3CCOCC3)n2)s1] | 5-(6-morpholino-4-(phenylsulfonyl)pyridin-2-yl)-4-(trifluoromethyl)thiazol-2-amine |

TABLE 1-continued
| Ex. # | Structure | Chemical Name |
|---|---|---|
| 7 | 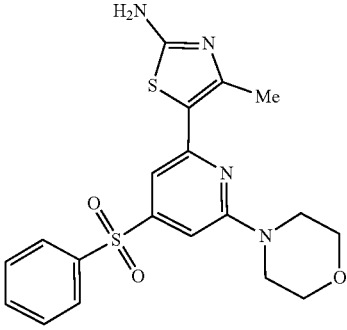 [SMILES: Cc1nc(N)sc1-c1cc(S(=O)(=O)c2ccccc2)cc(N2CCOCC2)n1] | 4-methyl-5-(6-morpholino-4-(phenylsulfonyl)pyridin-2-yl)thiazol-2-amine |
| 8 | 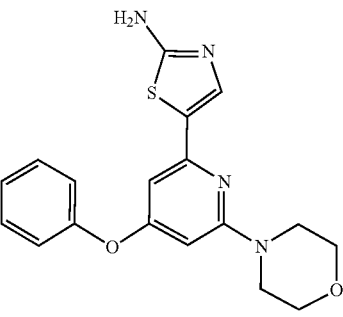 [SMILES: Nc1ncc(-c2cc(Oc3ccccc3)cc(N3CCOCC3)n2)s1] | 5-(6-morpholino-4-phenoxypyridin-2-yl)thiazol-2-amine |
| 9 | 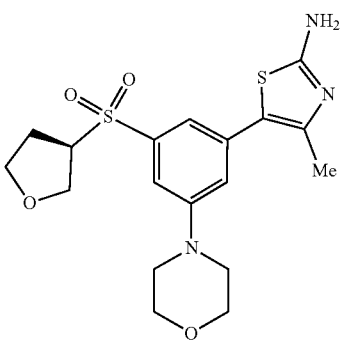 | (R)-4-methyl-5-(3-morpholino-5-((tetrahydrofuran-3-yl)sulfonyl)phenyl)thiazol-2-amine |
| 10 | 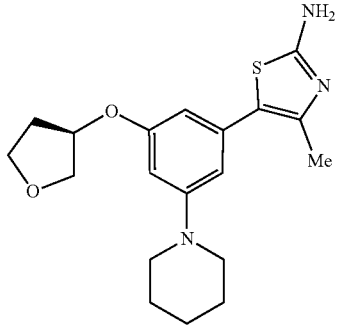 | (R)-4-methyl-5-(3-morpholino-5-((tetrahydrofuran-3-yl)oxy)phenyl)thiazol-2-amine |

TABLE 1-continued

| Ex. # | Structure | Chemical Name |
|---|---|---|
| 11 | 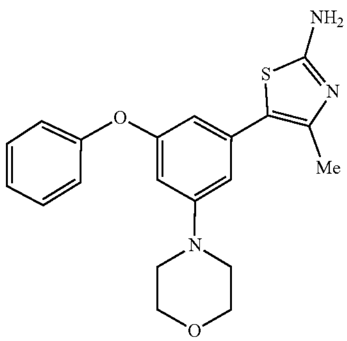 | 4-methyl-5-(3-morpholino-5-phenoxyphenyl)thiazol-2-amine |
| 12 | 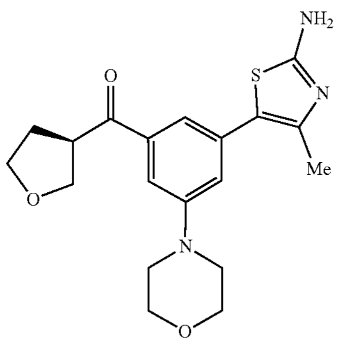 | (R)-(3-(2-amino-4-methylthiazol-5-yl)-5-morpholinophenyl)(tetrahydrofuran-3-yl)methanone |
| 13 | 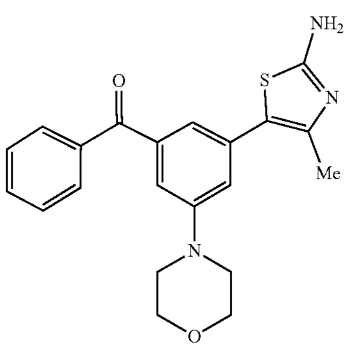 | (3-(2-amino-4-methylthiazol-5-yl)-5-morpholinophenyl)(phenyl)methanone |
| 14 | 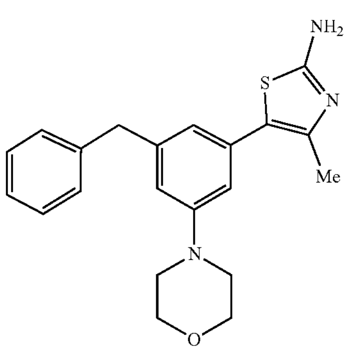 | 5-(3-benzyl-5-morpholinophenyl)-4-methylthiazol-2-amine |

TABLE 1-continued

| Ex. # | Structure | Chemical Name |
|---|---|---|
| 15 | 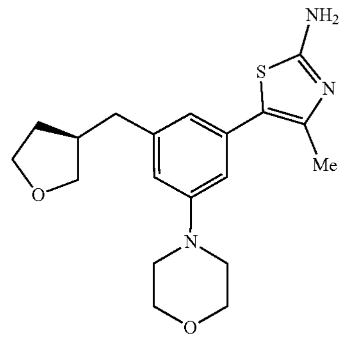 | (R)-4-methyl-5-(3-morpholino-5-((tetrahydrofuran-3-yl)methyl)phenyl)thiazol-2-amine |
| 16 | 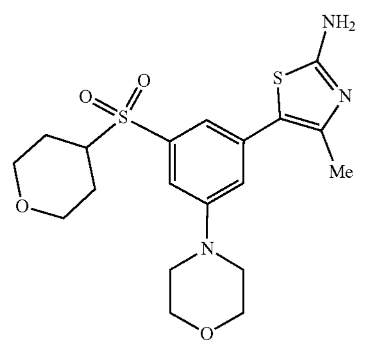 | 4-methyl-5-(3-morpholino-5-((tetrahydro-2H-pyran-4-yl)sulfonyl)phenyl)thiazol-2-amine |
| 17 | 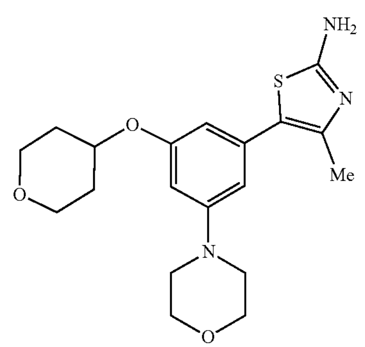 | 4-methyl-5-(3-morpholino-5-((tetrahydro-2H-pyran-4-yl)oxy)phenyl)thiazol-2-amine |
| 18 | 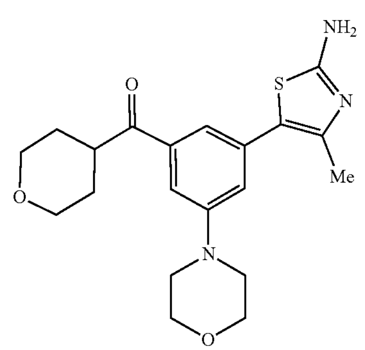 | (3-(2-amino-4-methylthiazol-5-yl)-5-morpholinophenyl)(tetrahydro-2H-pyran-4-yl)methanone |

TABLE 1-continued

| Ex. # | Structure | Chemical Name |
|---|---|---|
| 19 | | 4-methyl-5-(3-morpholino-5-((tetrahydro-2H-pyran-4-yl)methyl)phenyl)thiazol-2-amine | and pharmaceutically acceptable salts thereof.

Any formula given herein, such as Formula (I), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

The compounds of Formula (I) may be prepared and/or formulated as pharmaceutically acceptable salts. In some embodiments, pharmaceutically acceptable salts include acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methyl sulfonates, propyl sulfonates, besylates, xylenesulfonates, naphthalene-1-sulfonates, naphthalene-2-sulfonates, phenyl acetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimetharnine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include aluminum hydroxide, calcium hydroxide, potassium hydroxide, sodium carbonate, sodium hydroxide, and the like. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, benzenesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The embodiments also relate to pharmaceutically acceptable prodrugs of the compounds described herein, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The embodiments also relate to pharmaceutically active metabolites of compounds described herein, and uses of such metabolites in the methods provided herein. A "pharmaceutically active metabolite" means a pharmacologically active product of metabolism in the body of a compound described herein or salt thereof. Prodrugs and active metabolites of a compound may be determined using routine techniques known or available in the art. See, e.g., Bertolini et al., *J. Med Chem.* 1997, 40, 2011-2016; Shan et al., *J. Pharm. Set.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, a pharmaceutical composition according to the present disclosure comprises at least one compound of Formula (I), or a pharmaceutically acceptable salt thereof. The pharmaceutical compositions may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

As used herein, the terms "treat" or "treatment" is an approach for obtaining a beneficial or desired result, including clinical results. For purposes of this disclosure, beneficial or desired results include, but are not limited to: reducing the severity of or suppressing the worsening of an existing disease, symptom, or condition, alleviating a symptom and/or diminishing the extent of a symptom and/or preventing a worsening of a symptom associated with a condition, arresting the development of a disease, symptom, or condition, relieving the disease, symptom, or condition, causing regression of the disease, disorder, or symptom (in terms of severity or frequency of negative symptoms), or stopping the symptoms of the disease or condition. Beneficial or desired results can also be slowing, halting, or reversing the progressive course of a disease or condition.

The term "subject" refers to a mammalian patient in need of such treatment, such as a human. A "subject" may be a human, or may be a cat, dog, cow, rat, mouse, horse, or other domesticated mammal.

Exemplary conditions or diseases that may be therapeutic targets for modulators of the Vps34/PI3K III signaling pathway include diabetes, polycystic ovarian syndrome, diabetes-associated cardiovascular disease, neuro-inflammation, ischemic stroke and cancers including but not limited to glioblastoma, renal cell carcinoma, and melanoma. In some embodiments, the disease or medical condition is cancer, and the cancer is glioblastoma, renal cell carcinoma, or melanoma.

In one aspect, the compounds and pharmaceutical compositions described herein specifically target Vps34/PI3K III signaling pathway. In some embodiments, these compounds and pharmaceutical compositions can, by prevent, reverse, slow, or inhibit the Vps34/PI3K III signaling pathway. In some embodiments, the compounds and pharmaceutical compositions described herein are used in the treatment or prevention of diabetes, polycystic ovarian syndrome, diabetes-associated cardiovascular disease, cancer, neuro-inflammation or ischemic stroke. In some embodiments, the disease or medical condition is cancer, and the cancer is glioblastoma, renal cell carcinoma, or melanoma. In some embodiments, the methods of the present disclosure target diseases associated with the Vps34/PI3K III signaling pathway.

In the methods of the embodiments, an "effective amount" of a Vps34-PI3K modulator means an amount sufficient to alter the phosphorylation of constituents of the Vps34/PI3K III signaling pathway, alter expression of survival genes regulated by this pathway, improve cellular energetics, induce apoptosis in transformed cells, and inhibit autophagy. Measuring one or more of these markers of regulation of the Vps34/PI3K III signaling pathway may be performed by routine analytical methods such as those described below and is useful in a variety of settings, including in vitro assays.

In treatment methods according to the embodiments, an "effective amount" means an amount or dose sufficient to generally bring about the desired therapeutic benefit in subjects needing such treatment. Effective amounts or doses of the compounds of the embodiments may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of diseases or medical conditions associated with regulation of the Vps34/PI3K III signaling pathway. For example, additional active ingredients are those that are known or discovered to be effective in treating diseases or medical conditions associated with regulation of the Vps34/PI3K III signaling pathway, including those active against another target associated with the disease, such as but not limited to anticancer drugs with a synergistic mechanism, compounds that treat symptoms of such disorders, and anti-oxidants.

For example, additional active ingredients are those that are known or discovered to be effective in treating diseases or medical conditions associated with regulation of the Vps34/PI3K III signaling pathway, including those active against another target associated with the disease, such as but not limited to a) compounds that target different mechanisms of protein misfolding (such as aggregation and/or propagation); b) compounds that treat symptoms of such disorders (e.g., dopamine replacement therapies); and c) drugs that act as neuroprotectants by complementary mechanisms (e.g., those targeting autophagy, anti-oxidants, and adenosine A2A antagonists).

For example, compositions and formulations of the embodiments, as well as methods of treatment, can further comprise other drugs or pharmaceuticals, e.g., other active agents useful for treating or palliative for diabetes, polycystic ovarian syndrome, diabetes-associated cardiovascular disease, neuro-inflammation, ischemic stroke and cancers including but not limited to glioblastoma, renal cell carcinoma, and melanoma. In this regard, compositions and formulations of the generic and specific compounds described herein are useful in methods of treatment for diabetes, polycystic ovarian syndrome, diabetes-associated cardiovascular disease, neuro-inflammation, ischemic stroke and cancers including but not limited to glioblastoma, renal cell carcinoma, and melanoma. The pharmaceutical compositions of the embodiments may additional comprise one or more of such active agents, and methods of treatment may additionally comprise administering an effective amount of one or more of such active agents.

In some embodiments, the additional active agent is an anti-cancer agent, an anti-diabetic agent, or a cardiovascular drug. Exemplary anti-cancer agents include, but are not limited to, alkylating agents (e.g., cisplatin, chlorambucil, procarbazine, carmustine), antimetabolites (e.g., methotrexate, cytarabine, gemcitabine), anti-microtubule agents (e.g., methotrexate, cytarabine, gemcitabine), anti-tumor antibiotics (e.g., bleomycin, daunorubicin, doxorubicin, epirubicin, idarubicin, mitomycin, mitoxanthrone), topoisomerase inhibitors (e.g., etoposide, doxorubicin), mitotic inhibitors (e.g., paclitaxel, docetaxel, vinblastine, vincristine, vindesine, vinorelbine, colchicine, podophyllotoxin, griseofulvin, glaziovianin), corticosteroids (e.g., prednisone, prednisolone, methylprednisolone, dexamethasone), proteasome inhibitors (e.g., bortezomib, carfilzomib, Salinosporamide A (NPI-0052), MLN9708, CEP-18770, ONX 0912), kinase inhibitors (e.g., imatinib mesylate, gefltinib, erlotinib, lapatinib, canertinib, semaxinib, vatalanib, sorafenib, sutent, and leflunomide), histone-deacetylase inhibitors (e.g., suberoylanilide hydroxamic acid, chidamide, entinostat, mocetinostat, abexinostat, quisinostat, depsipeptide, resminostat, belinostat, CUDC-101, givinostat, panobinostat, pracinostat, SHP-141, teflnostat, trichostatin A, vorinostat, sulforaphane, pivanex, valproic acid) and antibodies (e.g., abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, ustekinumab). Exemplary anti-diabetic agents include, but are not limited to, biguanides (e.g., metformin, phenformin, and buformin), sulfonylureas (e.g., tolbutamide, acetohexamide, tolazamide, chlorpropamide, glipizide, glyburide or glibenclamide, glimepiride, gliclazide, glyclopyramide, and gliquidone), meglitinides (e.g., repaglinide and nateglinide), alpha-glucosidase inhibitors (e.g., miglitol, acarbose, and voglibose), thiazolidinediones (TZDs) (e.g., rosiglitazone, pioglitazone, and troglitazone), glucagonlike peptide-1 (GLP-1) agonists (e.g., exenatide, liraglutide, taspoglutide, and lixisenatide (Lyxumia)), dipeptidyl peptidase IV (DPP-4) inhibitors (e.g., vildagliptin (Galvus), sitagliptin (Januvia), saxagliptin (Onglyza), linagliptin (Tradjenta), alogliptin, septagliptin, Teneligliptin, and Gemigliptin: Zemiglo), selective sodium-glucose transporter-2 (SGLT-2) inhibitors (glycosurics) (e.g., dapagliflozin, canagliflozin, and empagliflozin), insulins (e.g., regular insulin (Humulin R, Novolin R), insulin lispro (Humalog), insulin aspart (Novolog), insulin glulisine (Apidra), prompt insulin zinc (Semilente), isophane insulin, neutral protamine Hagedom (NPH) (Humulin N, Novolin N), insulin zinc (Lente), extended insulin zinc insulin (Ultralente), insulin glargine (Lantus), and insulin detemir (Levemir)), amylinomimetics (e.g., pramlintide), bile acid sequestrants, and dopamine agonists. Exemplary cardiovascular drugs include, but are not limited to, anticoagulants (e.g., Rivaroxaban (Xarelto), Dabigatran (Pradaxa), Apixaban (Eliquis), Heparin (various), and Warfarin (Coumadin)), antiplatelet agents and dual antiplatelet therapy (DAPT) (e.g., aspirin, Clopidogrel (Plavix®), Dipyridamole, Prasugrel (Effient), and Ticagrelor (Brilinta)), angiotensin-converting enzyme (ACE) inhibitors (e.g., Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), and Trandolapril (Mavik)), angiotensin-2 Recepto antagonists (e.g., Candesartan (Atacand), Eprosartan (Teveten), Irbesartan (Avapro), Losartan (Cozaar), Telmisartan (Micardis), and Valsartan (Diovan)), angiotensin-receptor neprilysin inhibitors (ARNIs) (e.g., Sacubitril/valsartan (Entresto)), beta-andrenergic blocking agents (e.g., Acebutolol (Sectral), Atenolol (Tenormin), Betaxolol (Kerlone), Bisoprolol/hydrochlorothiazide (Ziac), Bisoprolol (Zebeta), Metoprolol (Lopressor, Toprol XL), Nadolol (Corgard), Propranolol (Inderal), and Sotalol (Betapace)), combined alpha and beta-blockers (e.g., carvedilol (Coreg) and labetalol hydrochloride (Normodyne, Trandate)), calcium channel blockers (e.g., Amlodipine (Norvasc, Lotrel), Diltiazem (Cardizem, Tiazac), Felodipine (Plendil), Nifedipine (Adalat, Procardia), Nimodipine (Nimotop), Nisoldipine (Sular), and Verapamil (Calan, Verelan)), cholesterol-lowering medications (e.g., Statins: Atorvastatin (Lipitor), Rosuvastatin (Crestor), Nicotinic Acids: Lovastatin (Advicor), and Cholesterol Absorption Inhibitors: Ezetimibe/Simvastatin (Vytorin)), digitoxins (e.g., lanoxin), diuretics (e.g., Amiloride (Midamor), Bumetanide (Bumex), Chlorothiazide (Diuril), Chlorthalidone (Hygroton), Furosemide (Lasix), Hydrochlorothiazide (Esidrix, Hydrodiuril), Indapamide (Lozol), and Spironolactone (Aldactone)), and vasodilators (e.g., Isosorbide dinitrate (Isordil), Nesiritide (Natrecor), Hydralazine (Apresoline), Nitrates, and Minoxidil).

In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present embodiments may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[1-

(phenylmethyl)piperidin-4-yl]-1-(2,3,4,5-tetrahydro-1H-1-benzazepin-8-yl)-1-propane fumarate), Metrifonate (T-588; (−)-R-alpha-[[2-(dimethylamino)ethoxy]methyl] benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyridine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate). Such a combination may serve to increase efficacy, ameliorate other disease symptoms, decrease one or more side effects, or decrease the required dose of an inventive compound. The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of Formula (I).

Methods of Use

The compounds and pharmaceutical compositions herein may be used to treat or prevent a disease or condition in an individual. In some embodiments, provided is a method of treating a disease or medical condition associated with regulation of the Vps34/PI3K III signaling pathway, comprising administering to a subject in need of such treatment an effective amount of at least one compound of Formula (I), or a compound of Table 1, or a pharmaceutically acceptable salt thereof; or a pharmaceutical composition comprising (a) at least one compound of Formula (I), or a compound of Table 1, or a pharmaceutically acceptable salt thereof, and (b) a pharmaceutically acceptable excipient.

In some embodiments, provided is a compound of Formula (I), or a compound of Table 1, or a pharmaceutically acceptable salt thereof; or a pharmaceutical composition comprising (a) at least one compound of Formula (I), or a compound of Table 1, or a pharmaceutically acceptable salt thereof, and (b) a pharmaceutically acceptable excipient, for use in the treatment of a disease or medical condition associated with regulation of the Vps34/PI3K III signaling pathway.

In some embodiments, provided is a use of at least one compound of Formula (I), or a compound of Table 1, or a pharmaceutically acceptable salt thereof; or a pharmaceutical composition comprising (a) at least one compound of Formula (I), or a compound of Table 1, or a pharmaceutically acceptable salt thereof, and (b) a pharmaceutically acceptable excipient, in the manufacture of a medicament for the treatment of a disease or medical condition associated with regulation of the Vps34/PI3K III signaling pathway.

In some embodiments, provided is a method of interfering with the Vps34/PI3K III signaling pathway in a cell, or modulating, preventing, slowing, reversing, or inhibiting of the Vps34/PI3K III signaling pathway in a cell, comprising contacting the cell with an effective amount of at least one compound of Formula (I), or a compound of Table 1, or a pharmaceutically acceptable salt thereof; and/or with at least one pharmaceutical composition comprising (a) at least one compound of Formula (I), or a compound of Table 1, or a pharmaceutically acceptable salt thereof, and (b) a pharmaceutically acceptable excipient, wherein the contacting is in vitro, ex vivo, or in vivo.

In some embodiments, the disease or medical condition is selected from diabetes, polycystic ovarian syndrome, diabetes-associated cardiovascular disease, neuro-inflammation, ischemic stroke, and cancers including but not limited to glioblastoma, renal cell carcinoma, and melanoma. In some embodiments, the disease or medical condition is selected from diabetes, polycystic ovarian syndrome, diabetes-associated cardiovascular disease, cancer, neuro-inflammation or ischemic stroke. In some embodiments, the disease or medical condition is cancer, and the cancer is glioblastoma, renal cell carcinoma, or melanoma.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a disease or medical condition described herein, and may also indicate directions for either in vivo or in vitro use.

In one aspect, provided herein are kits containing a compound or composition described herein and instructions for use. The kits may contain instructions for use in the treatment of a disease or medical condition associated with regulation of the Vps34/PI3K III signaling pathway in an individual in need thereof. A kit may additionally contain any materials or equipment that may be used in the administration of the compound or composition, such as vials, syringes, or IV bags. A kit may also contain sterile packaging.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

In some embodiments, compounds of the Formula (I) may be synthesized according to Scheme A.

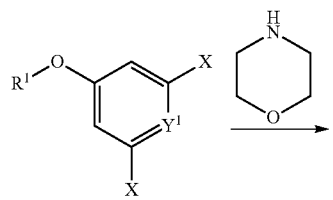

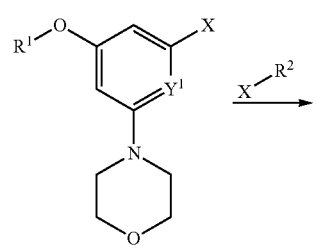

Scheme A

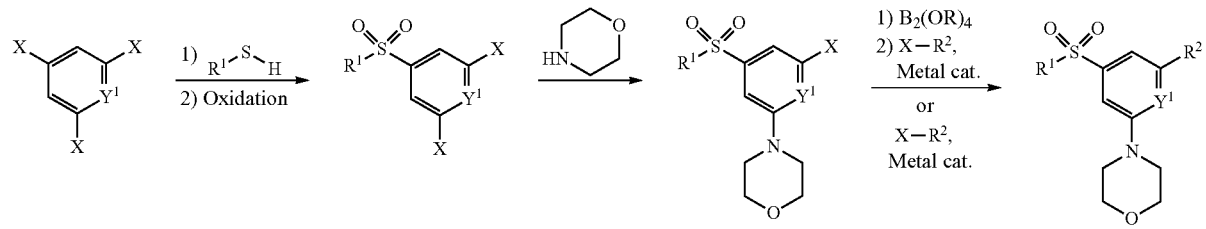

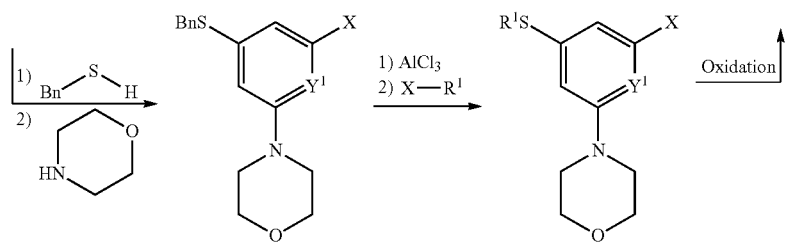

wherein $R^1$, $R^2$ and $Y^1$ are as defined for Formula (I), or any variation thereof detailed herein; and X is a halogen.

In some embodiments, compounds of Formula (I) may be synthesized according to Scheme B.

Scheme B

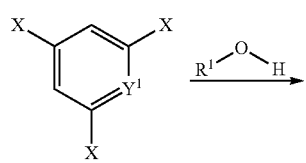

-continued

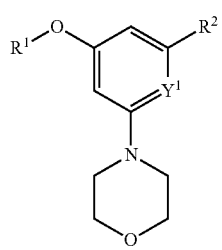

wherein $R^1$, $R^2$ and $Y^1$ are as defined for Formula (I), or any variation thereof detailed herein; and X is a halogen.

In some embodiments, compounds of the Formula (I) may be synthesized according to Scheme C.

Scheme C

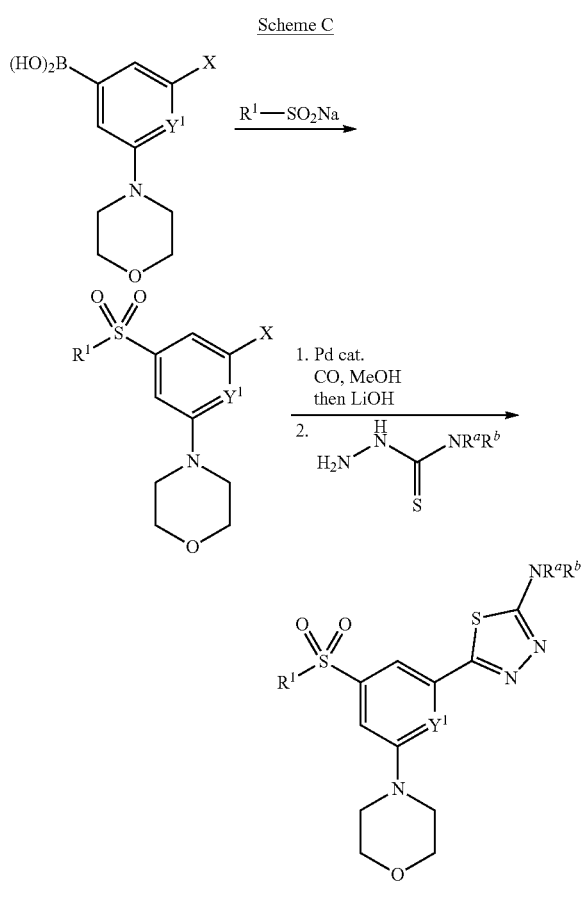

wherein $R^1$, $Y^1$, $R^a$ and $R^b$ are as defined for Formula (I), or any variation thereof detailed herein; and X is a halogen.

Chemical Synthesis

Exemplary chemical entities useful in methods of the present disclosure will now be described by reference to the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

EXAMPLES

The following examples are offered to illustrate but not to limit the present disclosure. One of skill in the art will recognize that the following synthetic reactions and schemes may be modified by choice of suitable starting materials and reagents in order to access other compounds of Formula (I). The compounds are prepared using the general methods described above.

The following abbreviations are used throughout the Examples: Boc (tert-butyloxycarbonyl), BINAP (2,2'-bis (diphenylphosphino)-1,1'-binaphthyl), CHAPS (3-[(3-cholamidopropyl)dimethylammonio]-1-propanesulfonate), DBU (1,8-Diazabicyclo[5.4.0]undec-7-ene), DIPEA (N,N-diisopropylethylamine), DMF (N,N-dimethylformamide), DMSO (dimethyl sulfoxide), DTT (1,4-dithiothreitol), EGTA (ethylene-bis(oxyethylenenitrilo)tetraacetic acid), HEPES (4-(2-hydroxyethyl)-1-piperazineethanesulfonic acid), mCPBA (meta-Chloroperoxybenzoic acid), MeOH (methanol), $Pd(dppf)Cl_2$ ([1,1'-bis(diphenylphosphino)ferrocene]palladium(II) dichloride), $Pd(OAc)_2$ (palladium(II) acetate), $Pd(PPh_3)_4$ (tetrakis(triphenylphosphine)palladium (O)), $PPh_3$ (triphenylphosphane), THF (tetrahydrofuran), TLC (thin layer chromatography), Tris-HCl (tris(hydroxymethyl)aminomethane hydrochloride) and Xantphos (4,5-Bis (diphenylphosphino)-9,9-dimethylxanthene).

Example 1: (R)-5-(3-morpholino-5-((tetrahydrofuran-3-yl)sulfonyl)phenyl)thiazol-2-amine Scheme 1

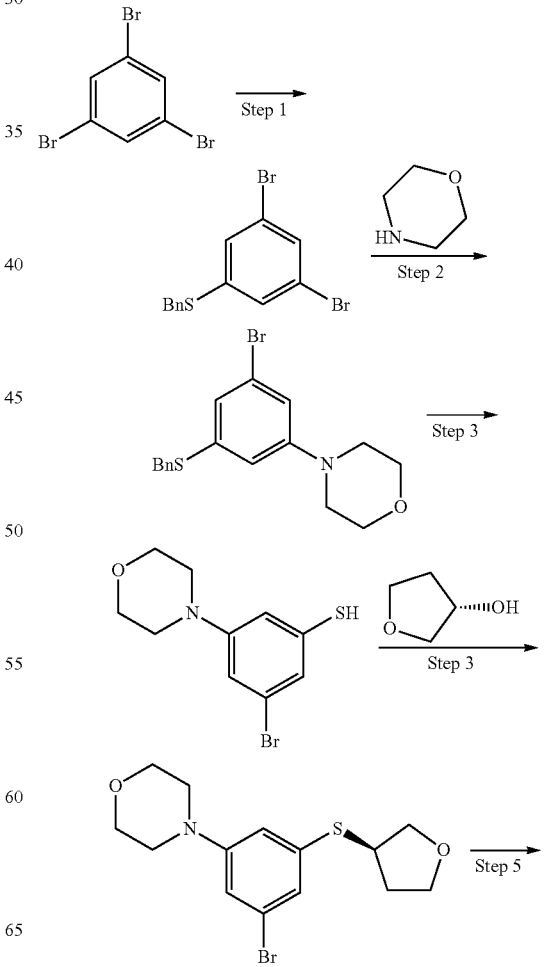

-continued

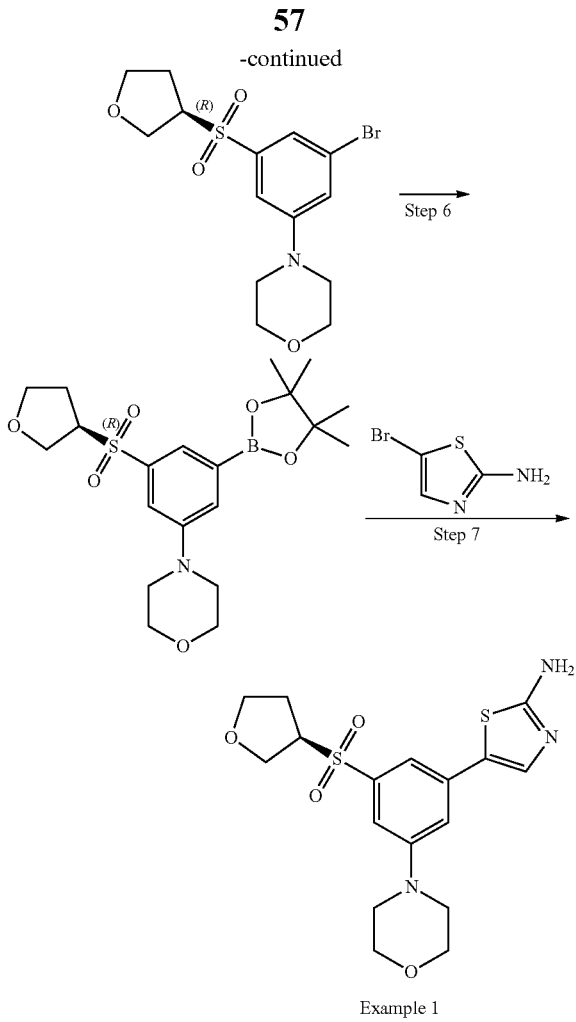

Example 1

Step 1: Phenylmethanethiol (19.8 g, 0.16 mol) was added to a solution of sodium hydride (7.04 g, 0.18 mol, 60% purity in mineral oil) in DMF (300 mL) at 0° C. The reaction was stirred for 15 min at room temperature and 1,3,5-tribromobenzene (50 g, 0.16 mol) was added. The reaction was stirred for another 2 hours at rt. The solution was poured into ice-water (500 mL) and extracted with ethyl acetate (300 mL×3). The organic extracts were combined, washed with brine (300 mL×2), dried over anhydrous sodium sulfate, and concentrated. The residue was purified by silica gel column chromatography (petroleum ether) to give benzyl(3,5-dibromophenyl)sulfane (50.1 g, 88% yield). The compound was confirmed with LC-MS only: 379.10 (M+Na)$^+$, $C_{13}H_{10}Br_2S$.

Step 2: $Pd_2dba_3$ (5 g) was added to a mixture of benzyl (3,5-dibromophenyl)sulfane (50 g, 0.14 mmol), BINAP (7.9 g, 12.6 mmol), t-BuONa (20.16 g, 0.21 mol), DBU (19.2 g, 0.126 mol), and morpholine (12.2 g, 0.14 mol) in toluene (400 mL) under nitrogen protection. The reaction was heated at 95° C. for 2 h. The mixture was cooled to room temperature and poured into water (500 mL). The mixture was extracted with ethyl acetate (300 mL×3). The organic extracts were combined, washed with brine (200 mL×2), dried over anhydrous sodium sulfate, and concentrated. The residue was purified by silica gel column chromatography (petroleum ether/ethyl acetate=30:1) to give 4-(3-(benzylthio)-5-bromophenyl)morpholine (21.3 g, 42% yield) as yellow solid. The compound was confirmed with LC-MS only: 364.30 (M+H)$^+$, $C_{17}H_{18}BrNOS$.

Step 3: Anhydrous $AlCl_3$ (60.7 g, 0.45 mol) was added to a solution of 4-(3-(benzylthio)-5-bromophenyl)morpholine (33 g, 0.09 mol) in toluene (500 mL). The reaction was heated at 50° C. for 2 h. The mixture was quenched with ice-water (500 mL) carefully and extracted with ethyl acetate (500 mL×3). The organic extracts were combined, washed with brine (300 mL×2), dried over anhydrous sodium sulfate, and concentrated. The residue was purified by silica gel column chromatography (petroleum ether/ethyl acetate=10:1) to give crude 3-bromo-5-morpholinobenzenethiol (21.6 g, 87% yield), which was used for next reaction without further purification. The compound was confirmed with LC-MS only: 276.22 (M+H)$^+$, $C_{10}H_{12}BrNOS$.

Step 4: DEAD (9.88 g, 56.7 mmol) was added to a solution of $PPh_3$ (14.9 g, 56.7 mmol) in toluene (100 mL) at 0° C. The solution was stirred for 0.5 hour at 0° C.—room temperature and a solution of (S)-tetrahydrofuran-3-ol (5.0 g, 56.7 mmol) in toluene (10 mL) was added. After stirring for another 0.5 hours at 0° C., a solution of 3-bromo-5-morpholino-benzenethiol (15.56 g, 56.75 mmol) in toluene (20 mL) was added. The reaction was further stirred for 1 hour at room temperature. The reaction solution was poured into water (200 mL) and extracted with ethyl acetate (200 mL×3). The combined organics were washed with brine (200 mL), dried over sodium sulfate, and concentrated to give a yellow solid. The crude was purified by silica gel column chromatography (petroleum ether/ethyl acetate=5:1) to give (R)-4-(3-bromo-5-((tetrahydrofuran-3-yl)thio)phenyl)morpholine (11.6 g, 59% yield) as pale yellow oil. The compound was confirmed with LC-MS only: 344.35 (M+H)$^+$, $C_{14}H_{18}O_2SBrN$.

Step 5: mCPBA (23.3 g, 0.13 mol) was added in portions to a solution of (R)-4-(3-bromo-5-((tetrahydrofuran-3-yl)thio)phenyl)morpholine (11.6 g, 33.7 mmol) in dichloromethane (250 mL). The mixture was stirred at room temperature for 2 h. 4,4,4',4',5,5,5',5'-Octamethyl-2,2'-bi(1,3,2-dioxaborolane) (34.2 g, 0.13 mol) was added and the resulting mixture was stirred for 0.5 hour at room temperature. The reaction mixture was washed with saturated $Na_2CO_3$ (200 mL×3), brine (100 mL), dried over sodium sulfate and concentrated. The crude was purified by silica gel column chromatography (petroleum ether/ethyl acetate=1:1) to give 4-[3-bromo-5-[(3R)-tetrahydrofuran-3-yl]sulfonyl-phenyl]morpholine (5.0 g, 39% yield) as a colorless oil. The compound was confirmed with LC-MS only: 376.53 (M+H)$^+$, $C_{14}H_{18}NO_4SBr$.

Step 6: A mixture of 4-[3-bromo-5-[(3R)-tetrahydrofuran-3-yl]sulfonyl-phenyl]morpholine (680 mg, 1.81 mmol, for preparation), 4,4,5,5-tetramethyl-2-(4,4,5,5-tetramethyl-1,3,2-dioxaborolan-2-yl)-1,3,2-dioxaborolane (689 mg, 2.72 mmol), KOAc (381 mg, 5.43 mmol), and Pd(dppf)$Cl_2$ (148 mg, 0.18 mmol) in 1,4-dioxane (20 mL) and DMSO (0.2 mL) was stirred at 100° C. for 1 hour under $N_2$. The reaction mixture was poured into water (50 mL) and extracted with dichloromethane (50 mL×3). The combined organics were washed with brine (20 mL), dried over sodium sulfate, and concentrated. The residue was purified by silica gel column chromatography (dichloromethane/methanol=100:1) to give 4-[3-[(3R)-Tetrahydrofuran-3-yl]sulfonyl-5-(4,4,5,5-tetramethyl-1,3,2-dioxaborolan-2-yl)phenyl]morpholine (400 mg, 52% yield) as an off-white solid.

Step 7: A mixture of 4-[3-[(3R)-tetrahydrofuran-3-yl]sulfonyl-5-(4,4,5,5-tetramethyl-1,3,2-dioxaborolan-2-yl)phenyl]morpholine (465 mg, 1.1 mmol), 5-bromothiazol-2-amine (196 mg, 1.1 mmol), $Na_2CO_3$ (350 mg, 3.3 mmol) and Pd(ddpf)$Cl_2$ (90 mg, 0.11 mmol) in 1,4-dioxane (15 mL) and H₂O (2 mL) was stirred at 100° C. for 2 hours under N₂. The reaction mixture was poured into water (50 mL) and extracted with dichloromethane (50 mL×3). The combined organics were washed with brine (30 mL), dried over sodium sulfate, and concentrated. The crude was purified by silica gel column chromatography (dichloromethane/methanol=100:1) and prep-TLC to afford (R)-5-(3-morpholino-5-((tetrahydrofuran-3-yl)sulfonyl)phenyl)thiazol-2-amine (21 mg, 5% yield) as an off-white solid. LC-MS: 396.00 (M+H)⁺, $C_{17}H_{21}N_3O_4S_2$. ¹H NMR (DMSO-d6, 400 MHz) δ: 7.61 (s, 1H), 7.32 (s, 2H), 7.26 (s, 1H), 7.18 (s, 1H), 7.14 (s, 1H), 4.37 (m, 1H), 4.01 (m, 1H), 3.82 (m, 2H), 3.76 (m, 4H), 3.64 (m, 1H), 3.25 (m, 4H), 1.95-2.16 (m, 2H).

Example 2: (R)-5-(3-morpholino-5-((tetrahydrofuran-3-yl)sulfonyl)phenyl)-4-(trifluoromethyl)thiazol-2-amine Example 2 was synthesized in the same manner as described for Example 1 in Scheme 1, but using 5-bromo-4-(trifluoromethyl)thiazol-2-amine (133 mg, 0.54 mmol) in step 7 to afford (R)-5-(3-morpholino-5-((tetrahydrofuran-3-yl)sulfonyl)phenyl)-4-(trifluoromethyl)thiazol-2-amine (71 mg, 28% yield) as an off-white solid. LC-MS: 464.1 (M+H)⁺, $C_{18}H_{20}F_3N_3O_4S_2$. ¹H NMR (DMSO-d6, 400 MHz) δ: 7.63 (s, 2H), 7.36 (s, 1H), 7.24 (s, 1H), 7.20 (s, 1H), 4.28 (m, 1H), 3.98 (m, 1H), 3.81 (m, 2H), 3.76 (m, 4H), 3.65 (m, 1H), 3.25 (m, 4H), 2.11 (m, 2H).

Example 3: 5-(3-morpholino-5-(phenylsulfonyl)phenyl)-1,3,4-thiadiazol-2-amine trifluoroacetic acid salt

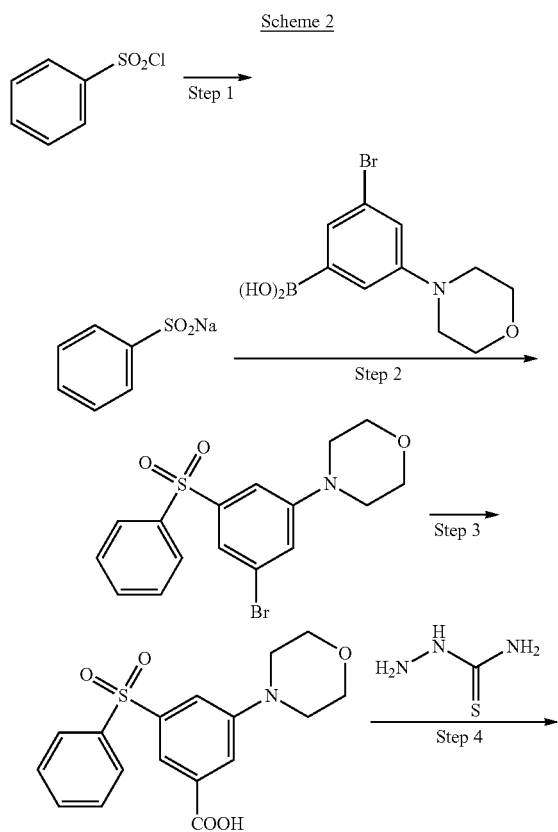

Scheme 2

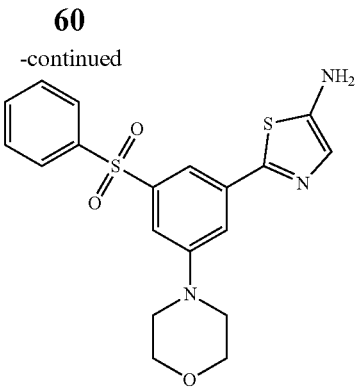

Example 3

Step 1: A mixture of benzenesulfonyl chloride (10 g, 56.7 mmol), sodium sulfite (14.3 g, 0.11 mol), and sodium bicarbonate (9.5 g, 0.11 mol) in water (100 mL) was stirred at 30° C. for 2 h. Water was removed in vacuo. The residue was extracted with methanol (30 mL×3). The organic extracts were combined, concentrated, and co-evaporated with dichloromethane for two times to give crude sodium benzenesulfinate (11 g, quantitative yield) as a white solid. The compound was confirmed with LC-MS only: 141.36 (M-Na)⁻ $C_6H_5NaO_2S$.

Step 2: Potassium carbonate (1.66 g, 12.0 mmol), 4 Å MS (0.5 g), and Cu(OAc)₂ (1.22 mg, 6.6 mmol) were added successively to a solution of sodium benzenesulfinate (0.98 g, 6.0 mmol) and 3-bromo-5-morpholinophenylboronic acid (2.56 g, 9.0 mmol) in DMSO (20 mL). The reaction was stirred for 2 hours at 45° C. in the presence of an oxygen balloon. The reaction mixture was poured into water (50 mL) and extracted with ethyl acetate (50 mL×3). The organic extracts were combined, washed with brine (20 mL), dried over anhydrous sodium sulfate, and concentrated. The residue was dissolved in dichloromethane (20 mL) and washed with 2 N NaOH (20 mL×2). The organic layer was dried over anhydrous sodium sulfate and concentrated. The resulting crude (1.03 g, yellow solid) was further triturated with a combination of petroleum ether/ethyl acetate (2/1, 20 mL ×2) to give 4-(3-bromo-5-(phenylsulfonyl)phenyl)morpholine (0.4 g, 18% yield) as pale yellow solid. The compound was confirmed with LC-MS only: 381.69 (M+H)⁺, $C_{16}H_{16}BrNO_3S$.

Step 3: A mixture of 4-(3-bromo-5-(phenylsulfonyl)phenyl)morpholine (1 g, 2.62 mmol), Pd(dppf)Cl₂ (0.2 g, 0.23 mmol), and Pd(OAc)₂ (60 mg, 0.28 mmol) in MeOH/DMF (10 mL/10 mL) was heated overnight at 80° C. in the presence of 20 kg of CO. Methanol was removed in vacuo. The residue was poured into water (20 mL) and extracted with ethyl acetate (20 mL×3). The organic extracts were combined, washed with brine (20 mL), dried over anhydrous sodium sulfate, and concentrated. The crude was purified by silica gel column chromatography (petroleum ether/ethyl acetate=10:1) to give methyl ester (0.61 g, 64% yield). A solution of the methyl ester (600 mg, 1.66 mmol) and LiOH.H₂O (133 mg, 2.32 mmol) in THF/water (3 mL/3 mL) was stirred for 1 hour at 60° C. THF was removed in vacuo and the water phase was acidified to pH=3-4 with 5% KHSO₄. The resulting mixture was extracted with dichloromethane (20 mL×3). The organic extracts were combined, dried over anhydrous sodium sulfate, and concentrated to give crude 3-morpholino-5-(phenylsulfonyl)benzoic acid (0.4 g, 69% yield), which was used for the next reaction without further purification. The compound was confirmed with LC-MS only: 348.18 (M+H)$^+$, $C_{17}H_{17}NO_5S$.

Step 4: 3-Morpholino-5-(phenylsulfonyl)benzoic acid (370 mg, 1.07 mmol) was dissolved in POCl$_3$ (4 mL), and hydrazinecarbothioamide (194 mg, 2.13 mmol) was added. The reaction was stirred for 30 min at 85° C. The reaction mixture was cooled to room temperature and added to water (40 mL), keeping the internal temperature below 60° C. The mixture was cooled to room temperature and neutralized to pH 8-9 with sodium carbonate. The resulting precipitate was collected and washed with a combination of petroleum ether/ethyl acetate (1/2, 20 mL ×2). The cake was re-purified by prep-HPLC to afford 5-(3-morpholino-5-(phenylsulfonyl)phenyl)-1,3,4-thiadiazol-2-amine trifluoroacetic acid salt (45 mg, 10% yield). LC-MS: 403.1 (M+H)$^+$, $C_{18}H_{18}N_4O_3S_2$. $^1$H NMR (DMSO-d6, 400 MHz) δ: 8.03 (d, J=8.4 Hz, 2H), 7.60-7.78 (m, 6H), 7.45 (s, 1H), 7.41 (s, 1H), 3.75 (m, 4H), 3.27 (m, 4H).

Example 4: 5-(3-morpholino-5-(phenylsulfonyl)phenyl)-1,2,4-thiadiazol-3-amine

Scheme 3

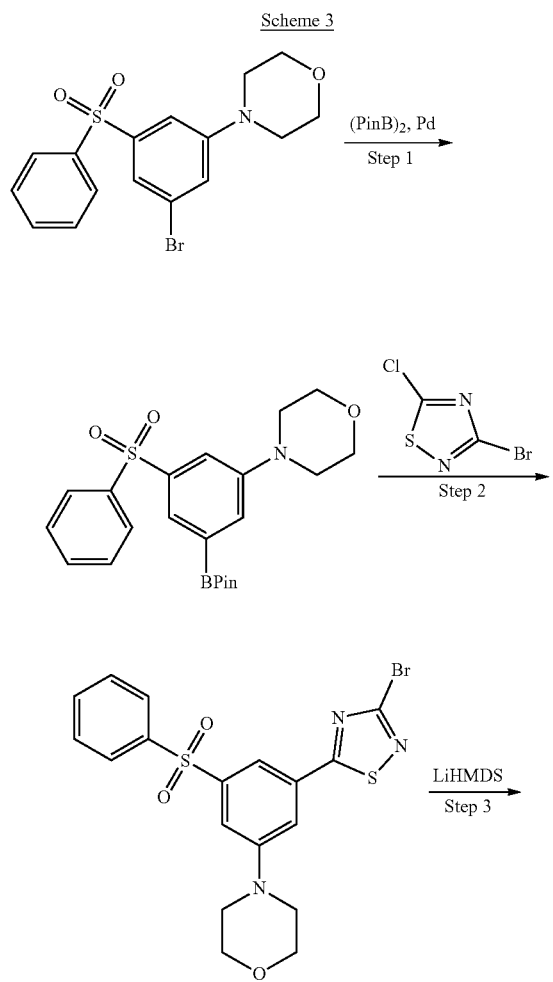

-continued

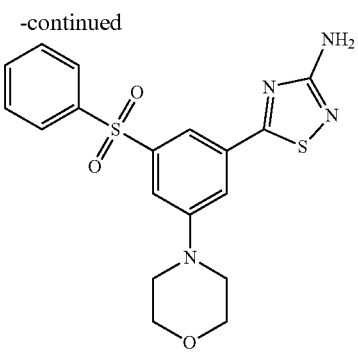

Example 4

Step 1: A mixture of potassium acetate (82 mg, 2.49 mmol), 4,4,4',4',5,5,5',5'-Octamethyl-2,2'-bi(1,3,2-dioxaborolane) (318 mg, 1.25 mmol), Pd(dppf)Cl$_2$ (68 mg, 0.08 mmol), and 4-(3-bromo-5-(phenylsulfonyl)phenyl)morpholine (300 mg, 0.83 mmol, for preparation, see Scheme 2) in dioxane/DMSO (5 mL/0.05 mL) was heated at 100° C. for 1 h. The reaction mixture was poured into water (50 mL) and extracted with ethyl acetate (50 mL×3). The organic extracts were combined, washed with brine (20 mL), dried over anhydrous sodium sulfate, and concentrated. The residue was purified by silica gel column chromatography (petroleum ether/ethyl acetate=5:1) to give 4-(3-(phenylsulfonyl)-5-(4,4,5,5-tetramethyl-1,3,2-dioxaborolan-2-yl)phenyl)morpholine (250 mg, 70% yield). The compound was confirmed with LC-MS only: 429.90 (M+H)$^+$, $C_{22}H_{28}BNO_5S$.

Step 2: A mixture of 4-(3-(phenylsulfonyl)-5-(4,4,5,5-tetramethyl-1,3,2-dioxaborolan-2-yl)phenyl)morpholine (250 mg, 0.58 mmol), 3-bromo-5-chloro-1,2,4-thiadiazole (96 mg, 0.48 mmol), Pd(dppf)Cl$_2$ (20 mg, 0.03 mmol), and CsF (146 mg, 0.96 mmol) in dioxane/water (10 mL/1 mL) was heated overnight at 80° C. The reaction mixture was poured into water (50 mL) and extracted with ethyl acetate (50 mL×3). The organic extracts were combined, washed with brine (20 mL), dried over anhydrous sodium sulfate, and concentrated. The residue was purified by silica gel column chromatography (petroleum ether/ethyl acetate=10:1) to give 4-(3-(3-bromo-1,2,4-thiadiazol-5-yl)-5-(phenylsulfonyl)phenyl)morpholine (203 mg, 91% yield). The compound was confirmed with LC-MS only: 466.17 (M+H)$^+$, $C_{18}H_{16}BrN_3O_3S_2$.

Step 3: LiHMDS (1 M in THF, 1.23 mL, 1.23 mmol) was added to a solution of 4-(3-(3-bromo-1,2,4-thiadiazol-5-yl)-5-(phenylsulfonyl)phenyl)morpholine (190 mg, 0.41 mmol) in THF (10 mL) at 0° C. The reaction mixture was warmed to room temperature and stirred for 1 h. Water (20 mL) was added and the mixture was stirred at room temperature for 3 h. The reaction mixture was diluted with saturated NH$_4$Cl (10 mL) and extracted with ethyl acetate (30 mL×3). The organic extracts were combined, dried over anhydrous sodium sulfate, and concentrated. The residue was purified by silica gel column chromatography (petroleum ether/ethyl acetate=5:1) to afford 5-(3-morpholino-5-(phenylsulfonyl)phenyl)-1,2,4-thiadiazol-3-amine (89 mg, 54% yield). LC-MS: 403.1 (M+H)$^+$, $C_{18}H_{18}N_4O_3S_2$. $^1$H NMR (DMSO-d6, 400 MHz) δ: 8.04 (d, J=7.6 Hz, 2H), 7.72 (m, 2H), 7.64 (m, 2H), 7.59 (s, 1H), 7.53 (s, 1H), 6.95 (s, 2H), 3.76 (m, 4H), 3.29 (m, 4H).

Example 5: 5-(6-morpholino-4-(phenylsulfonyl)pyridin-2-yl)thiazol-2-amine

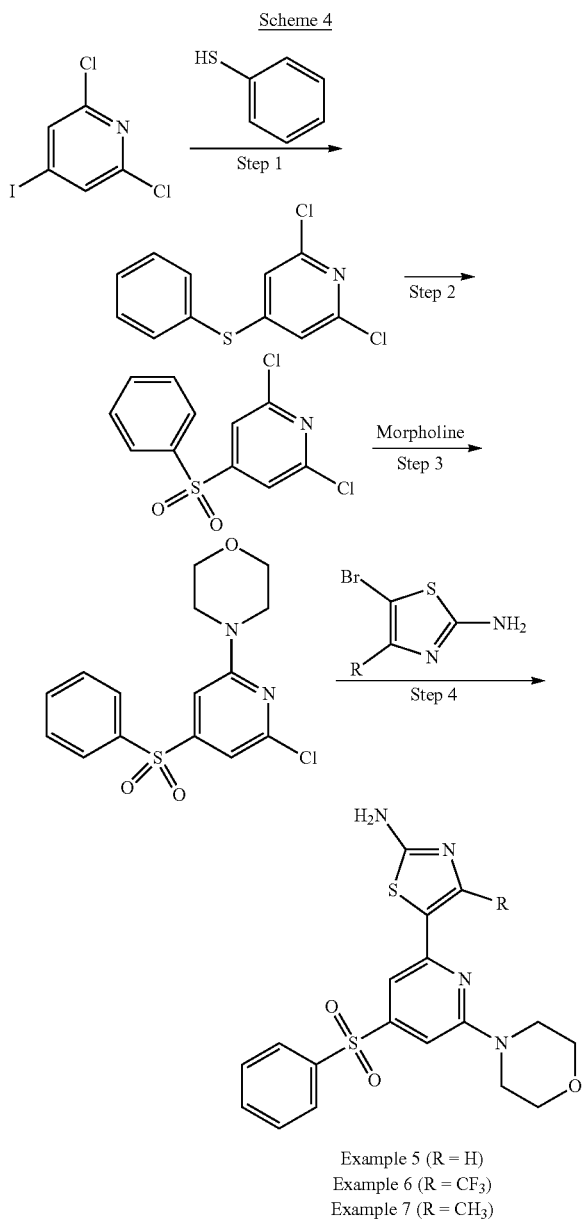

Example 5 (R = H)
Example 6 (R = CF3)
Example 7 (R = CH3)

Step 1: Pd$_2$(dba)$_3$ (0.17 g, 0.18 mmol) was added to a mixture of 2,6-dichloro-4-iodopyridine (1 g, 3.66 mmol), thiophenol (0.44 g, 4.03 mmol), Xantphos (0.21 g, 0.37 mmol), and DIPEA (0.94 g, 7.32 mmol) in dioxane (20 mL) under N$_2$. The reaction was heated at 110° C. for 2 h. The mixture was cooled to room temperature, poured into water (20 mL), and extracted with ethyl acetate (20 mL×3). The combined organics were washed with brine (20 mL), dried over sodium sulfate, and concentrated. The residue was purified by silica gel column chromatography (petroleum ether) to give 2,6-dichloro-4-(phenylthio)pyridine (0.78 g, 83% yield) as off-white solid. The compound was confirmed with LC-MS only: 256.16 (M+H)$^+$, C$_{11}$H$_7$Cl$_2$NS.

Step 2: mCPBA (1.84 g, 10.7 mmol) was added portionwise to a solution of 2,6-dichloro-4-(phenylthio)pyridine (0.68 g, 2.67 mmol) in dichloromethane (20 mL). The mixture was stirred for 50 min at rt. The reaction mixture was washed with sat. Na$_2$CO$_3$ (10 mL×2), brine (20 mL), dried over sodium sulfate, and concentrated. The crude was purified by silica gel column chromatography (petroleum ether/ethyl acetate=60:1) to give 2,6-dichloro-4-(phenylsulfonyl)pyridine (0.69 g, 90% yield). The compound was confirmed with LC-MS only: 287.98 (M+H)$^+$, C$_{11}$H$_7$Cl$_2$NO$_2$S.

Step 3: A solution of 2,6-dichloro-4-(phenylsulfonyl)pyridine (0.69 g, 2.40 mmol), morpholine (0.23 g, 2.64 mmol), and DIPEA (0.40 g, 3.13 mmol) in dioxane (20 mL) was heated at 120° C. overnight. The reaction was cooled to room temperature and poured into water (100 mL). The mixture was extracted with ethyl acetate (100 mL×3). The organic extracts were combined, dried over sodium sulfate, and concentrated. The crude was purified by silica gel column chromatography (petroleum ether/ethyl acetate=60:1) to give 4-(6-chloro-4-(phenylsulfonyl)pyridin-2-yl)morpholine (700 mg, 86% yield). The compound was confirmed with LC-MS only: 339.74 (M+H)$^+$, C$_{15}$H$_{15}$ClN$_2$O$_3$S.

Step 4: A mixture of 4-(6-chloro-4-(phenylsulfonyl)pyridin-2-yl)morpholine (270 mg, 0.80 mmol), 5-bromothiazol-2-amine (156 mg, 0.80 mmol), 1,1,1,2,2,2-hexamethyldistannane (557 mg, 2.0 mmol), and anhydrous LiCl (33 mg, 0.80 mmol) in 1,4-dioxane (10 mL) was degassed and protected with nitrogen. Pd(PPh$_3$)$_4$ (93 mg, 0.08 mmol) was added and the reaction was stirred at 90° C. for 3 hours under nitrogen protection. The reaction mixture was poured into water (20 mL) and extracted with ethyl acetate (20 mL×3). The combined organics were washed with brine (20 mL), dried over sodium sulfate, concentrated. The crude was purified by a silica gel column chromatography (dichloromethane/ethyl acetate=10:1) and prep-TLC to afford 5-(6-morpholino-4-(phenylsulfonyl)pyridin-2-yl)thiazol-2-amine (Example 5) (29 mg, 9% yield) as yellow solid. LC-MS: 403.1 (M+H)$^+$, C$_{18}$H$_{18}$N$_4$O$_3$S$_2$. $^1$H NMR (DMSO-d6, 400 MHz) δ: 8.07 (d, J=1.6 Hz, 2H), 7.85 (s, 1H), 7.73 (m, 1H), 7.65 (m, 2H), 7.36-7.55 (m, 3H), 6.91 (s, 1H), 3.69 (m, 4H), 3.51 (m, 4H).

Example 6: 5-(6-morpholino-4-(phenylsulfonyl)pyridin-2-yl)-4-(trifluoromethyl)thiazol-2-amine 5-(6-morpholino-4-(phenylsulfonyl)pyridin-2-yl)-4-(trifluoromethyl)thiazol-2-amine (5 mg, 2% yield) was obtained from 4-(6-chloro-4-(phenylsulfonyl)pyridin-2-yl)morpholine (203 mg, 0.60 mmol) and 5-bromo-4-(trifluoromethyl)thiazol-2-amine (148 mg, 0.60 mmol) following the same procedure as Example 5 (Scheme 4, step 4). LC-MS: 468.75 (M−H)$^−$, C$_{19}$H$_{17}$F$_3$N$_4$O$_3$S$_2$. $^1$H NMR (CDCl$_3$, 400 MHz) δ: 7.95 (d, J=7.6 Hz, 2H), 7.65 (m, 1H), 7.58 (m, 2H), 7.33 (s, 2H), 7.22 (s, 1H), 7.05 (s, 1H), 3.82 (m, 4H), 3.59 (m, 4H).

Example 7: 4-methyl-5-(6-morpholino-4-(phenylsulfonyl)pyridin-2-yl)thiazol-2-amine 4-methyl-5-(6-morpholino-4-(phenylsulfonyl)pyridin-2-yl)thiazol-2-amine (31 mg, 7% yield) was obtained from 4-(6-chloro-4-(phenylsulfonyl)pyridin-2-yl)morpholine (338 mg, 1.0 mmol) and 5-bromo-4-methylthiazol-2-amine (384 mg, 2.0 mmol) following the same procedure as Example 5 (Scheme 4, step 4). LC-MS: 417.3 (M+H)$^+$, C$_{19}$H$_{20}$N$_4$O$_3$S$_2$. $^1$H NMR (DMSO-d6, 400 MHz) δ: 8.04 (d, J=7.2 Hz, 2H), 7.74 (m, 1H), 7.66 (m, 2H), 7.31 (s, 2H), 6.97 (s, 1H), 6.94 (s, 1H), 3.69 (m, 4H), 3.51 (m, 4H), 2.35 (s, 3H).

Example 8: 5-(6-morpholino-4-phenoxypyridin-2-yl)thiazol-2-amine

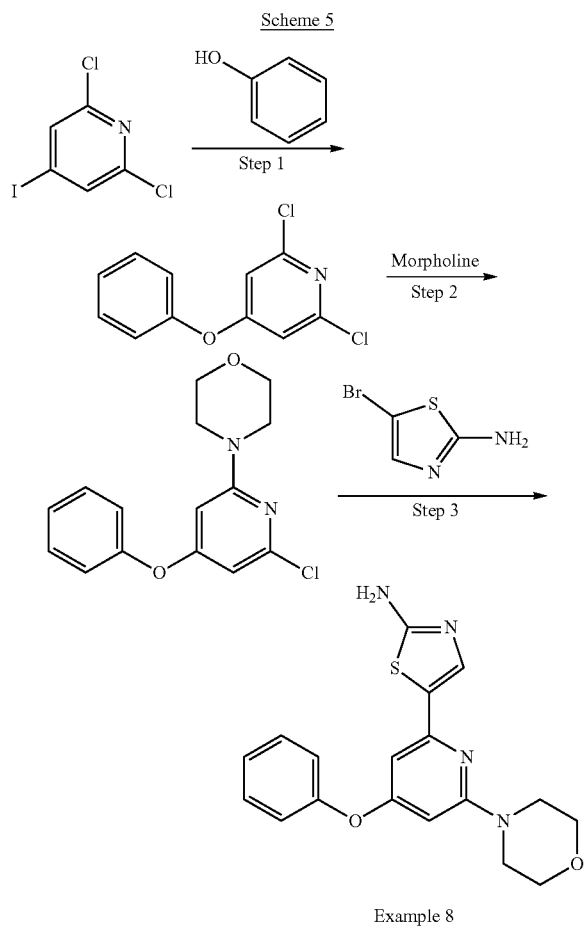

Example 8

Step 1: A mixture of 2,6-dichloro-4-iodopyridine (600 mg, 2.20 mmol), phenol (207 mg, 2.20 mmol), and potassium carbonate (455 mg, 3.30 mmol) in DMSO (20 mL) was stirred at 100° C. for 3 hours under $N_2$. The reaction mixture was poured into water (100 mL) and extracted with ethyl acetate (100 mL×3). The combined organics were washed with brine (50 mL×2), dried over sodium sulfate, and concentrated. The residue was purified by silica gel column chromatography (petroleum ether) to give 2,6-dichloro-4-phenoxypyridine, (210 mg, 40% yield). The compound was confirmed with LC-MS only: 239.86 $(M+H)^+$, $C_{11}H_7Cl_2NO$.

Step 2: A solution of 2,6-dichloro-4-phenoxypyridine (200 mg, 0.84 mmol), morpholine (218 mg, 2.51 mmol), and DIPEA (216 mg, 1.67 mmol) in 1,4-dioxane (6 mL) was heated overnight at 140° C. under nitrogen protection. The solvent was removed in vacuo. The residue was treated with water (30 mL) and extracted with ethyl acetate (30 mL×3). The combined organics were washed with brine (20 mL), dried over sodium sulfate, and concentrated. The residue was purified by silica gel column chromatography (petroleum ether/ethyl acetate=100:1) to give 4-(6-Chloro-4-phenoxypyridin-2-yl)morpholine (180 mg, 74% yield). The compound was confirmed with LC-MS only: 290.75 $(M+H)^+$, $C_{15}H_{15}ClN_2O_2$.

Step 3: 5-(6-morpholino-4-phenoxypyridin-2-yl)thiazol-2-amine (15 mg, 10% yield) was obtained from 4-(6-chloro-4-phenoxypyridin-2-yl)morpholine (129 mg, 0.44 mmol, for preparation) and 5-bromothiazol-2-amine (157 mg, 0.88 mmol) following the same procedure as example 5 (Scheme 4, step 4). LC-MS: 354.92 $(M+H)^+$, $C_{18}H_{18}N_4O_2S$. 1H NMR (400 MHz, Chloroform-d) 1H NMR (400 MHz, Chloroform-d) δ 7.46-7.34 (m, 3H), 7.22 (t, J=7.4 Hz, 1H), 7.09 (dd, J=7.5, 1.6 Hz, 2H), 6.48 (d, J=1.7 Hz, 1H), 5.98 (d, J=1.7 Hz, 1H), 5.60-5.31 (m, 2H), 3.83-3.77 (m, 4H), 3.45 (t, J=4.9 Hz, 4H).

Biological Assay

Assay Example 1: VPS34 Protocol

The PI3KC3 (hVPS34) kinase reactions utilize ATP and produce ADP as a byproduct. The ADP production is quantified by ADP-Glo luminescence detection. The PI3KC3 (hVPS34) kinase assay was performed by Reaction Biology Corp. (Malvern, Pa.).

This was a 3-step reaction: First, the kinase reaction with lipid substrate was carried out in the presence of ATP. The reaction was then quenched, and the remaining ATP depleted with ADP-Glo™ reagent. Finally, the ADP was converted to ATP, which is measured using a luciferase/luciferin reaction. The luminescence was converted into μM ADP production based on ADP standard curves. The nonlinear regression to obtain the standard curve and $IC_{50}$ values were performed using Graphpad Prism software.

The substrate (Phosphatidylinositol (PI): Phosphatidylserine (PS)) was added to freshly prepared reaction buffer (40 mM Tris-HCl (pH7.5), 3 μM Orthovanadate, 20 mM $MgCl_2$, 2 mM DTT, 0.05% CHAPS, 1% DMSO). The PI3KC3 (hVPS34) kinase was delivered into the substrate solution with gentle mixing. Compounds were delivered in 100% DMSO into the kinase reaction mixture by Acoustic technology (Echo550; nanoliter range). The reaction was incubated for 20 min at room temperature. ATP was delivered into the reaction mixture to initiate the reaction. After incubating the mixture for 60 min at 30° C., the reaction was quenched with ADP-Glo reagent (Promega ADP Glo Kinase Assay kit #V9102) and incubated for 40 min at room temperature. Detection mixture (Promega ADP Glo Kinase Assay kit #V9102) was added and the reaction was incubated for 30 minutes. Luminescence was measured.

$IC_{50}$ values for compounds against PI3KC3 (hVPS34) kinase are presented in Table 2.

TABLE 2

| Ex. # | VPS34 $IC_{50}$ (μM) |
| --- | --- |
| 1 | 3.8 |
| 2 | 2.1 |
| 3 | 1.6 |
| 4 | 2.2 |
| 5 | 0.081 |
| 6 | 0.287 |
| 7 | 0.019 |
| 8 | 0.15 |

Assay Example 2: PI3Kα Protocol

Inhibition of PI3Kα—Quantification of ATP to ADP conversion as a measure of PI3Kα activity. Active PI3Kα (Life Technologies), in the presence or absence of PI3Kα inhibitor, was reacted with PIP2:PS (Life Technologies), a substrate specifically optimized for use with Class I PI3 kinases, and ultrapure ATP (Promega). The conversion of ATP to ADP by PI3Kα was measured as luminescence signal via Promega ADP-Glo kinase activity assay. Assay was validated using published PI3Kα inhibitors LY294002, PI-103, BYL719, and GDC0198 as well as a DMSO vehicle control.

Compounds were prepared at 100× final concentration using a 12-point, 1:3 serial-dilution in DMSO, with DMSO control as the 12$^{th}$ point. Compound was then diluted in HEPES buffer (25 mM HEPES pH 7.5, 1 mM EGTA, 0.3% CHAPS) prior to addition to PI3Kα. Active PI3Kα diluted to 0.24 ng/μL (1.1 nM) in (50 mM HEPES pH 7.5, 6 mM MgCl$_2$, 1 mM EGTA, 200 mM NaCl, 0.03% CHAPS, 8 mM DTT) was incubated with compound for 0 hr and 3 hr prior to the start of the reaction. 25 μM PIP2:PS and 60 μM ATP were diluted from stock solution (25 mM HEPES pH 7.5, 1 mM EGTA, 0.3% CHAPS) and added to initiate the PI3Kα reaction. Reaction time was 30 minutes. ATP to ADP conversion was measured in Luminescence Counts on DTX880 Plate Reader (Beckman Coulter). The IC$_{50}$ of the compounds were reported using the GraphPad Prism software. Analytical method was non-linear regression, 4-parameter curve fit with bottom fit to validated PI3Kα inhibitor reference controls and no top fit (floating top).

IC$_{50}$ values for compounds against PI3Kα are presented in Table 3.

TABLE 3

| Ex. # | PI3Kα IC$_{50}$ (μM) |
| --- | --- |
| 1 | 0.75 |
| 2 | 0.74 |
| 3 | 2.2 |
| 4 | 11.2 |
| 5 | 0.5019 |
| 6 | 5.243 |
| 7 | 2.3 |
| 8 | 3.418 |

The invention claimed is:

1. A compound of Formula I:

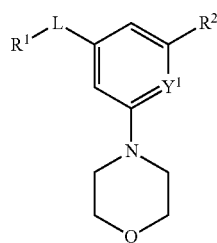

(I)

wherein
R$^1$ is C$_6$-C$_{14}$ aryl, 5- to 10-membered heteroaryl, C$_3$-C$_6$ cycloalkyl, or 4- to 10-membered heterocycloalkyl, wherein the C$_6$-C$_{14}$ aryl, 5- to 10-membered heteroaryl, C$_3$-C$_6$ cycloalkyl, or 4- to 10-membered heterocycloalkyl of R$^1$ are each unsubstituted or substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^a$, —SR$^a$, —S(O)$_2$R$^a$, —NR$^b$R$^c$, —C(O)R$^a$, —OC(O)R$^a$, —C(O)OR$^a$, —C(O)NR$^b$R$^c$, —OC(O)NR$^b$R$^c$, —NR$^a$C(O)R$^b$, —NR$^a$C(O)OR$^b$, substituted or unsubstituted C$_3$-C$_6$ cycloalkyl, substituted or unsubstituted C$_3$-C$_6$ cycloalkenyl, substituted or unsubstituted C$_6$-C$_{14}$ aryl, substituted or unsubstituted 5- to 10-membered heteroaryl, and substituted or unsubstituted 4- to 10-membered heterocycloalkyl;

L is —S(O)$_2$—, —O—, —C(O)— or CH$_2$—;
Y$^1$ is CH or N;
R$^2$ is a 5-membered heteroaryl or a 5-membered heterocycloalkyl, wherein the 5-membered heteroaryl and 5-membered heterocycloalkyl of R$^2$ are each unsubstituted or substituted with one or more substituents selected from the group consisting of halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, C$_1$-C$_6$ haloalkyl, —OR$^d$, —SR$^d$, —S(O)$_2$R$^d$, —NR$^e$R$^f$, —C(O)R$^d$, —OC(O)R$^d$, —C(O)OR$^d$, —C(O)NR$^e$R$^f$, —OC(O)NR$^e$R$^f$, —NR$^d$C(O)R$^e$, —NR$^d$C(O)OR$^e$, substituted or unsubstituted C$_3$-C$_6$ cycloalkyl, substituted or unsubstituted C$_3$-C$_6$ cycloalkenyl, substituted or unsubstituted C$_6$-C$_{14}$ aryl, substituted or unsubstituted 5- to 10-membered heteroaryl, and substituted or unsubstituted 4- to 10-membered heterocycloalkyl; and
R$^a$, R$^b$, R$^c$, R$^d$, R$^e$, and R$^f$ are each independently H or C$_{1-4}$ alkyl;
wherein when L is —S(O)$_2$— and Y$^1$ is N, R$^1$ is not 4,4-difluoro-piperidin1-yl;
or a pharmaceutically acceptable salt thereof.

2. The compound of claim 1, or a pharmaceutically acceptable salt thereof, wherein R$^1$ is C$_6$-C$_{14}$ aryl or 4- to 10-membered heterocycloalkyl.

3. The compound of claim 1, or a pharmaceutically acceptable salt thereof, wherein R$^1$ is phenyl.

4. The compound of claim 1, or a pharmaceutically acceptable salt thereof, wherein R$^1$ is 5- or 6-membered heterocycloalkyl.

5. The compound of claim 1, or a pharmaceutically acceptable salt thereof, wherein R$^1$ is tetrahydrofuranyl, tetrahydropyranyl, pyrrolidinyl, piperidinyl, piperazinyl, or morpholinyl.

6. The compound of claim 5, or a pharmaceutically acceptable salt thereof, wherein R$^1$ is tetrahydrofuran-3-yl.

7. The compound of claim 5, or a pharmaceutically acceptable salt thereof, wherein R$^1$ is tetrahydropyran-4-yl.

8. The compound of claim 1, or a pharmaceutically acceptable salt thereof, wherein L is —S(O)$_2$—.

9. The compound of claim 1, or a pharmaceutically acceptable salt thereof, wherein L is —O—.

10. The compound of claim 1, or a pharmaceutically acceptable salt thereof, wherein L is —C(O)—.

11. The compound of claim 1, or a pharmaceutically acceptable salt thereof, wherein L is —CH$_2$—.

12. The compound of claim 1, or a pharmaceutically acceptable salt thereof, wherein Y$^1$ is CH.

13. The compound of claim 1, or a pharmaceutically acceptable salt thereof, wherein Y$^1$ is N.

14. The compound of claim 1, or a pharmaceutically acceptable salt thereof, wherein R$^2$ is a 5-membered heteroaryl ring.

15. The compound of claim 1, or a pharmaceutically acceptable salt thereof, wherein R$^2$ is a 5-membered heteroaryl ring substituted with one or more substituents selected from the group consisting of C$_{1-6}$ alkyl, C$_{1-6}$ haloalkyl and NR$^e$R$^f$, wherein R$^e$ and R$^f$ are independently H or C$_{1-4}$ alkyl.

16. The compound of claim 1, wherein R$^2$ is thiazolyl or thiadiazolyl substituted with one or more substituents selected from the group consisting of $C_{1-6}$ alkyl, $C_{1-6}$ haloalkyl and $NR^eR^f$, wherein $R^e$ and $R^f$ are independently H or $C_{1-4}$ alkyl.

17. The compound of claim 1, wherein $R^2$ is thiazolyl or thiadiazolyl substituted with one or more substituents selected from the group consisting of methyl, $CF_3$ and $NH_2$.

18. The compound of claim 1, or a pharmaceutically acceptable salt thereof, wherein $R^2$ is:

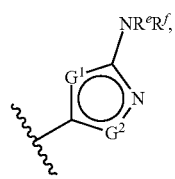

wherein $G^1$ is S or N;

$G^2$ is $CR^3$, S, or N;

$R^3$ is H, $C_{1-6}$ alkyl or $C_{1-6}$ haloalkyl; and $R^e$ and $R^f$ are independently H or $C_{1-4}$ alkyl.

19. The compound of claim 18, or a pharmaceutically acceptable salt thereof, wherein $G^1$ is S and $G^2$ is $CR^3$.

20. The compound of claim 19, or a pharmaceutically acceptable salt thereof, wherein $R^3$ is H.

21. The compound of claim 19, or a pharmaceutically acceptable salt thereof, wherein $R^3$ is $C_{1-6}$ alkyl.

22. The compound of claim 19, or a pharmaceutically acceptable salt thereof, wherein $R^3$ is $C_{1-6}$ haloalkyl.

23. The compound of claim 18, or a pharmaceutically acceptable salt thereof, wherein $G^1$ is N and $G^2$ is S.

24. The compound of claim 18, or a pharmaceutically acceptable salt thereof, wherein $G^1$ is S and $G^2$ is N.

25. The compound of claim 1, or a pharmaceutically acceptable salt thereof, wherein Re and $R^f$ are both H.

26. A compound selected from the group consisting of:

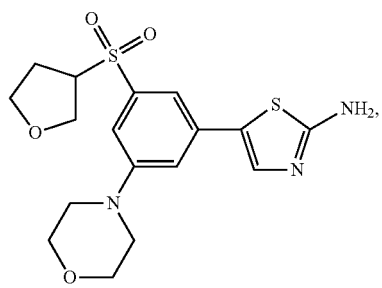

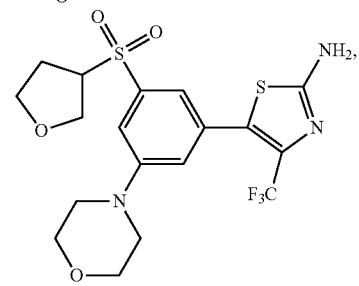

-continued

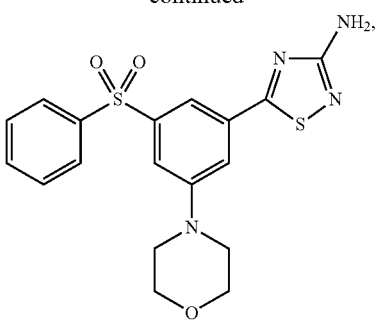

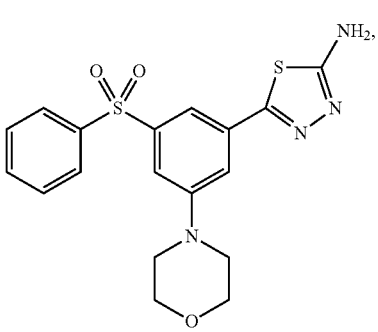

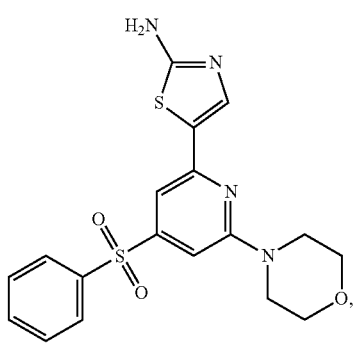

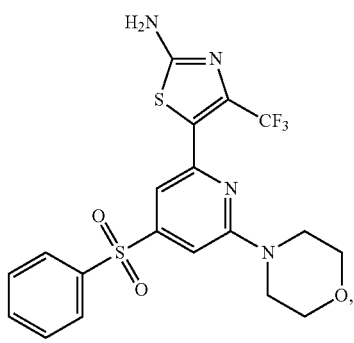

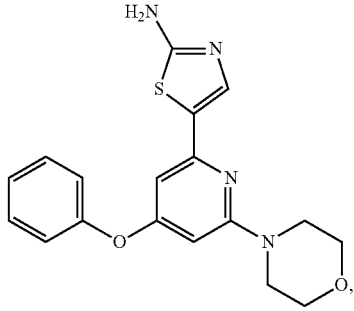

71
-continued
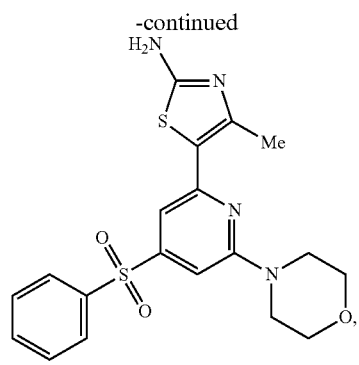
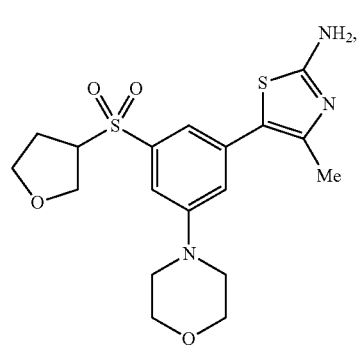
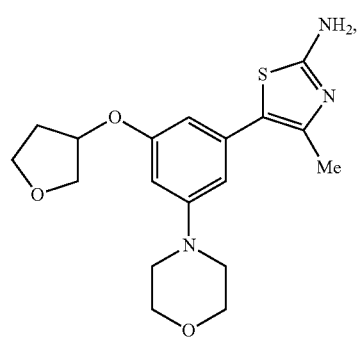
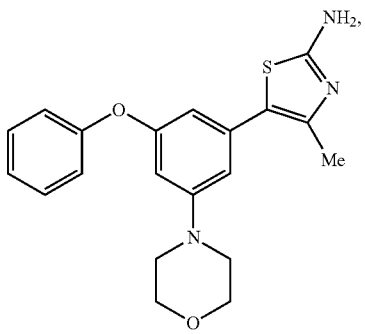
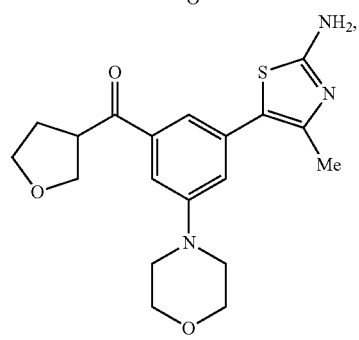
72
-continued
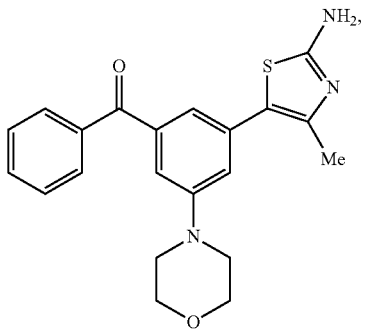
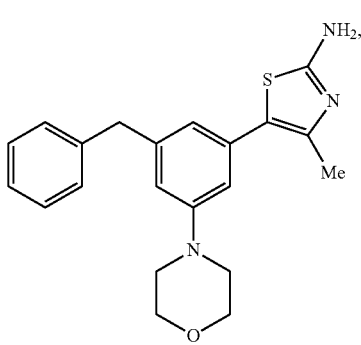
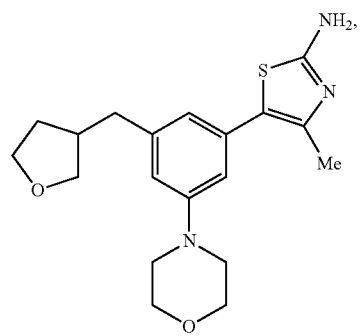
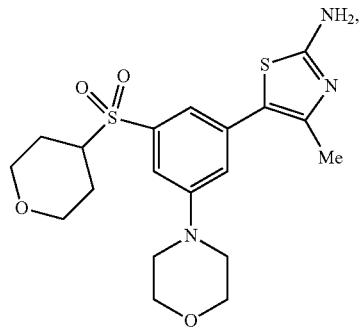
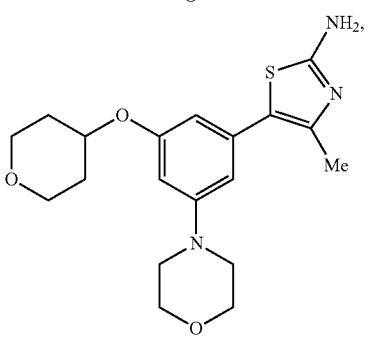

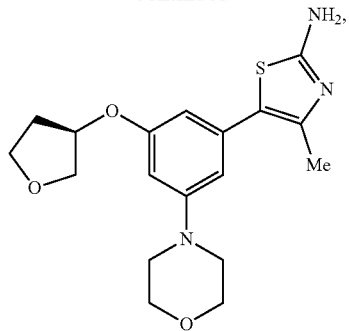 [SMILES: Cc1nc(N)sc1-c1cc(C[C@@H]2CCOC2)cc(N2CCOCC2)c1]
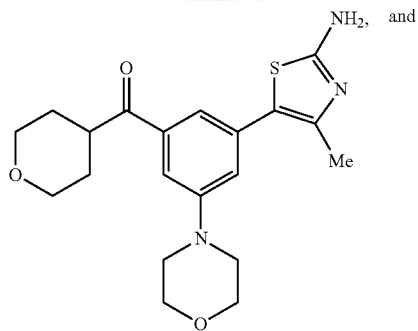
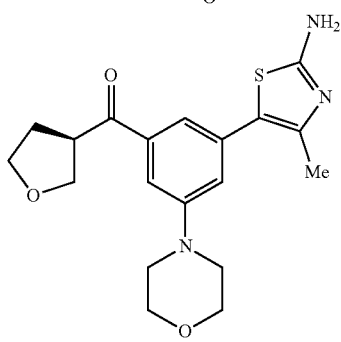
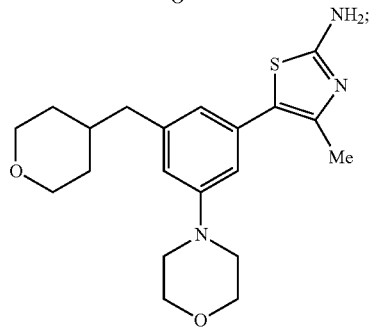
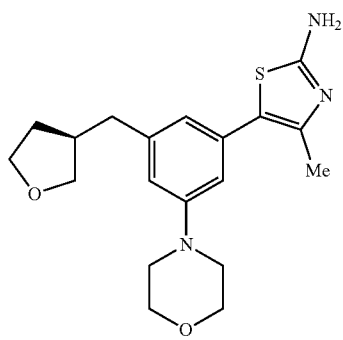
or a pharmaceutically acceptable salt thereof.
27. The compound of claim 26, wherein the compound is selected from the group consisting of:
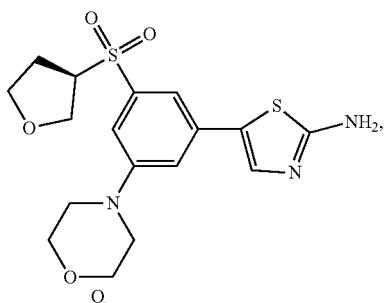
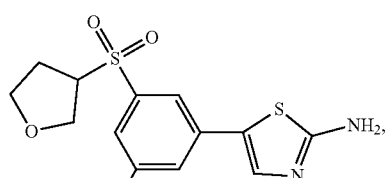
or a pharmaceutically acceptable salt thereof.
28. A compound selected from the group consisting of:
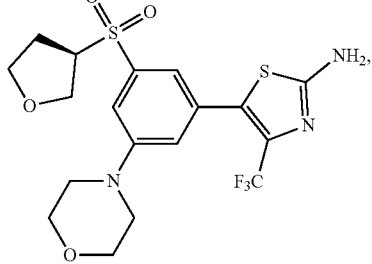
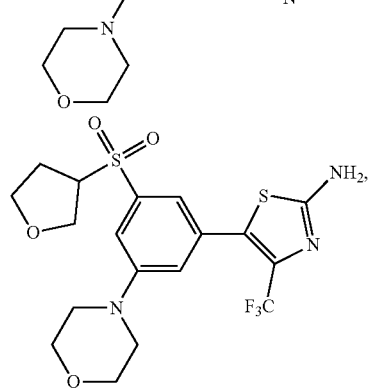
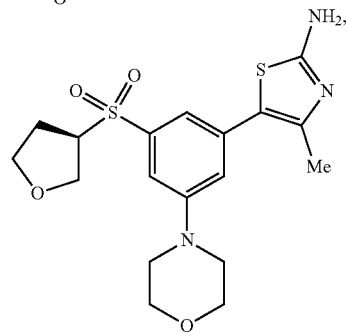

-continued

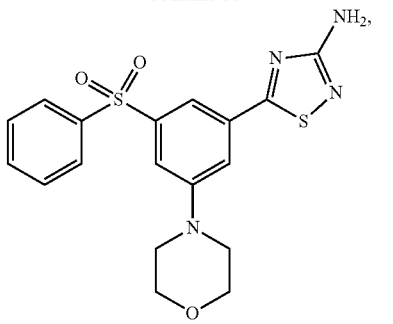

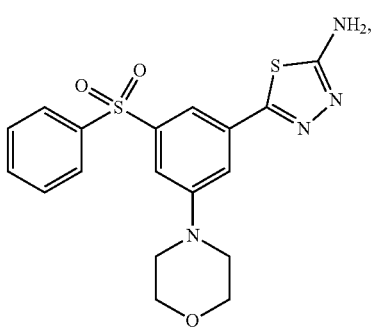

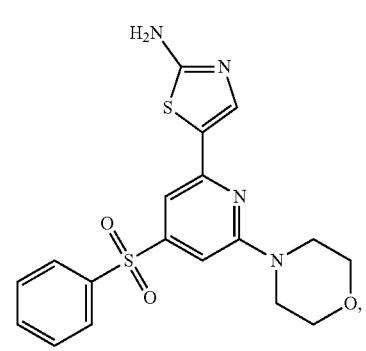

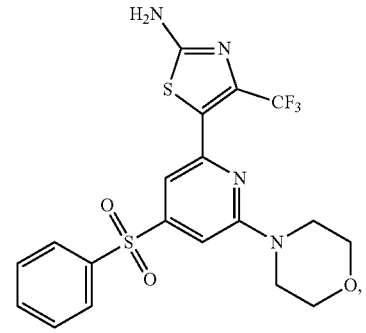

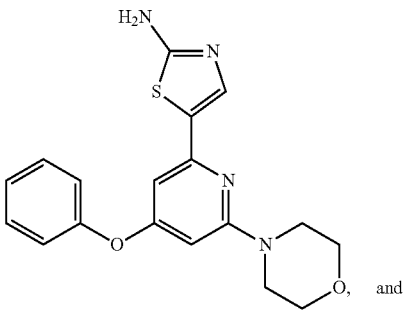

-continued

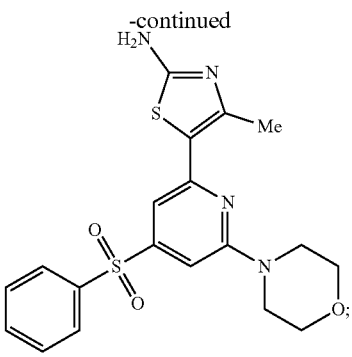

or a pharmaceutically acceptable salt thereof.

29. The compound of claim 28, wherein the compound is selected from the group consisting of:

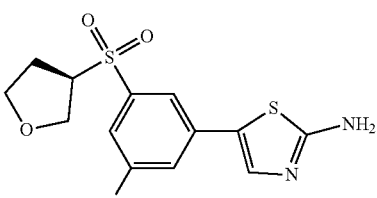

and

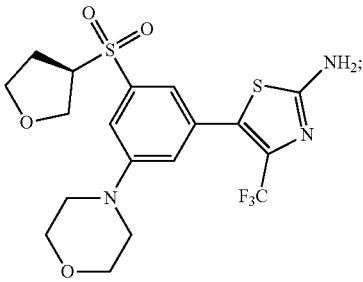

or a pharmaceutically acceptable salt thereof.

30. A pharmaceutical composition comprising (a) at least one compound of claim 1, or a pharmaceutically acceptable salt thereof, and (b) a pharmaceutically acceptable excipient.

31. A method of treating a disease or medical condition associated with regulation of the Vps34/PI3K III signaling pathway, comprising administering to a subject in need of such treatment an effective amount of at least one compound of claim 1, or a pharmaceutically acceptable salt thereof.

32. The method of claim 31, wherein the disease or medical condition is diabetes, polycystic ovarian syndrome, diabetes-associated cardiovascular disease, cancer, neuro-inflammation or ischemic stroke.

33. The method of claim 32, wherein the disease or medical condition is cancer, and the cancer is glioblastoma, renal cell carcinoma, or melanoma.

34. A method of interfering with the Vps34/PI3K III signaling pathway in a cell, or modulating, preventing, slowing, reversing, or inhibiting of the Vps34/PI3K III signaling pathway in a cell, comprising contacting the cell with an effective amount of at least one compound according to claim 1, or a pharmaceutically acceptable salt thereof, wherein the contacting is in vitro, ex vivo, or in vivo.

* * * * *